US012631634B2

(12) United States Patent
Feng et al.

(10) Patent No.: US 12,631,634 B2
(45) Date of Patent: May 19, 2026

(54) HISTOCHEMICAL AND CYTOCHEMICAL METHODS FOR DETECTING NTRK FUSION PROTEINS

(71) Applicant: Ventana Medical Systems, Inc., Tucson, AZ (US)

(72) Inventors: Janine Feng, New York, NY (US); Frances Hansen, Tucson, AZ (US); Linda Kivi, Marana, AZ (US); Patricia Nuzzo, Tucson, AZ (US); John Palting, Tucson, AZ (US); John Pate, Oro Valley, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 1271 days.

(21) Appl. No.: 17/249,762

(22) Filed: Mar. 11, 2021

(65) Prior Publication Data

US 2021/0199655 A1     Jul. 1, 2021

Related U.S. Application Data

(63) Continuation of application No. PCT/EP2019/074463, filed on Sep. 13, 2019.

(60) Provisional application No. 62/731,032, filed on Sep. 13, 2018.

(51) Int. Cl.
| | |
|---|---|
| *G01N 33/566* | (2006.01) |
| *G01N 1/30* | (2006.01) |
| *G01N 33/574* | (2006.01) |

(52) U.S. Cl.
CPC ............. *G01N 33/566* (2013.01); *G01N 1/30* (2013.01); *G01N 33/57484* (2013.01); *G01N 2001/302* (2013.01)

(58) Field of Classification Search
CPC .. G01N 33/566; G01N 1/30; G01N 33/57484; G01N 2001/302
USPC ........................................ 435/7.23
See application file for complete search history.

(56) References Cited

U.S. PATENT DOCUMENTS

| | | |
|---|---|---|
| 2015/0073036 A1 | 3/2015 | Hawryluk et al. |
| 2017/0103521 A1 | 4/2017 | Chukka et al. |
| 2017/0234886 A1 | 8/2017 | Smith et al. |

FOREIGN PATENT DOCUMENTS

| | | |
|---|---|---|
| JP | 2017509871 A | 2/2014 |
| WO | 2015017533 A1 | 2/2015 |
| WO | 2016089853 A1 | 6/2016 |
| WO | 2018055014 A1 | 3/2018 |
| WO | 2018118786 A1 | 6/2018 |

OTHER PUBLICATIONS

Almagro & Fransson, Frontiers in Bioscience 2008; 13:1619-33.*
De Genst et al., Dev Comp Immunol 2006; 30:187-98.*
Yoshinaga et al., J. Biochem 2008; 143: 593-601.*
Amatu et al., NTRK gene fusions as novel targets of cancer therapy across multiple tumour types, ESMO Open, 2016, doi:10.1136/esmoopen-2015-000023, 9 pages, vol. 1, Issue 2, e000023.
Argani, P. et al., Detection of the ETV6-NTRK3 Chimeric RNA of Infantile Fibrosarcoma/Cellular Congenital Mesoblastic Nephroma in Paraffin-Embedded Tissue: Application to Challenging Pediatric Renal Stromal Tumors, Modern Pathology, 2000, pp. 29-36, 13(1).
Bailey, J. et al., Tropomyosin receptor kinase inhibitors: an updated patent review for 2010-2016—Part II, Expert Opinion on Therapetuic Patents, Mar. 2017, pp. 831-849, vol. 27, Issue 7.
Barbacid, M. et al., The trk family of tyrosine protein kinase receptors, Biochim. Biophys. Acta Rev. Cancer, 1991, pp. 115-127, 1072.
Barbacid, M., Structural and Functional Properties of the TRK Family of Neurotrophin Receptors, Annals New York Academy of Sciences, 1995, pp. 442-458.
Bishop, J. A. et al., Utility of mammaglobin immunohistochemistry as a proxy marker for the ETV6-NTRK3 translocation in the diagnosis of salivary mammary analogue secretory carcinoma, Human Pathology, 2013, pp. 1982-1988, 44.
Bourgeois, J.M. et al., Molecular Detection of the ETV6-NTRK3 Gene Fusion Differentiates Congenital Fibrosarcoma From Other Childhood Spindle Cell Tumors, American Journal of Surgical Pathology, 2000, pp. 937-946. 24(7).
Brzezianska, E. et al., Molecular analysis of the RET and NTRK1 gene rearrangements in papillary thyroid carcinoma in the Polish population, Mutation Research, 2006, pp. 26-35, 599.
D'Amico et al, State of the art in antigen retrieval for immunohistochemistry, Journal of Immunological Methods, 2009, pp. 1-18, vol. 341, Elsevier.
De Braud, F. G., et al., Alka-372-001: First-in-human, phase I study of entrectinib—an oral pan-trk, ROS1, and ALK inhibitor—in patients with advanced solid tumors with relevant molecular alterations (Abstract), 2014 ASCO Annual Meeting, 2014, 1 page, Abstract 2502.
Eide, F., et al., Naturally Occurring Truncated trkB Receptors Have Dominant Inhibitory Effects on Brain-Derived Neurotrophic Factor Signaling, Journal of Neuroscience, May 15, 1996, pp. 3123-3129, 16(10).

(Continued)

*Primary Examiner* — Yan Xiao
(74) *Attorney, Agent, or Firm* — Charney IP Law LLC; Thomas M. Finetti

(57) ABSTRACT

Materials and methods for detecting NTRK rearrangements via affinity staining. Samples are stained with a biomarker-specific reagent (such as an antibody) that binds to a retained portion of TrkA, TrkB, and/or TrkC. The staining pattern is evaluated, and the presence of a Trk fusion is determined by detecting whether or not the sample has at least a threshold number of cells having a threshold staining intensity. In some cases, the same scoring methodology is applied regardless of the staining localization pattern. In other cases, a cytoplasmic and/or membranous localization is scored by a first methodology, whereas a nuclear localization is scored by a second methodology. The methods disclosed herein may be applied across non-endocrine solid tumor types.

20 Claims, 8 Drawing Sheets
(4 of 8 Drawing Sheet(s) Filed in Color)

Specification includes a Sequence Listing.

(56)           References Cited

OTHER PUBLICATIONS

Farago, A. F. et al., Clinicopathologic Features of Non-Small-Cell Lung Cancer Harboring an NTRK Gene Fusion, JCO Precision Oncology, Jul. 23, 2018, pp. 1-12.

Feng, J. et al: "TRK wild-type and fusion protein expression in solid tumors: characterizationby inmunohistochemistry and in situ hybridisation" , Dec. 31, 2018 (Dec. 31, 2018), XP002795727, Retrieved from the Internet: URL:https://www.loxooncology.com/docs/presentations/Loxo-RTD MAP Poster -Pan-TRK.pdf [retrieved on Nov. 19, 2019J, 1 page.

Fernandez-Cuesta, L. et al., Abstract 1531: Cross-entity mutation analysis of lung neuroendocrine tumors sheds light into their molecular origin and identifies new therapeutic targets, 105th Annual Meeting of the American Association for Cancer Research, 2014, San Diego, California, AACR, 1 page.

Gatalica, Z. et al., Molecular characterization of cancers with NTRK gene fusions, Modern Pathology, Aug. 31, 2018, 7 pages, published online https://doi.org/10.1038/s41379-018-0118-3.

Hechman, J.F., et al., Pan-Trk Immunohistochemistry Is an Efficient and Reliable Screen for the Detection of NTRK Fusions, Am J Surg Pathol, Nov. 1, 2017, pp. 1547-1551, vol. 41, No. 11.

Hung, Y.P., et al., Evaluation of pan-TRK immunohistochemistry in infantile fibrosarcoma, lipofibromatosis-like neural tumour and histological mimics, Histopathology, Jun. 4, 2018, pp. 634-644, vol. 73, No. 4.

International Search and Written Opinion mailed Dec. 3, 2019 in connection with PCT/EP2019/074463 filed Sep. 13, 2019, 17 pages.

Klein, R. et al., The trkB Tyrosine Protein Kinase Is a Receptor for Brain-Derived Neurotrophic Factor and Neurotrophin-3, Cell, Jul. 26, 1991, pp. 395-403, vol. 66.

Leeman-Neill, R. J. et al., ETV6-NTRK3 Is a Common Chromosomal Rearrangement in Radiation-Associated Thyroid Cancer, Cancer, Mar. 15, 2014, pp. 799-807, 120 (6).

Lemmon, M. et al., Cell Signaling by Receptor Tyrosine Kinases, Cell, 2010, pp. 1117-1134, 141.

Luberg, K. et al., Novel transcripts reveal a complex structure of the human TRKA gene and imply the presence of multiple protein isoforms, BMC Neuroscience, 2015, pp. 1-21, 16:78.

Murphy, D.A., et al., Detecting Gene Rearrangements in Patient Populations Through a 2-Step Diagnostic Test Comprised of Rapid IHC Enrichment Followed by Sensitive Next-Generation Sequencing, Appl Immunohistochem Mol Morphol, Aug. 1, 2017, pp. 513-523, vol. 25, No. 7.

Prichard, J. W., Overview of Automated Immunohistochemistry, Arch Pathol Lab Med, (2014), pp. 1578-1582, vol. 138.

Ross, J. S. et al., New Routes to Targeted Therapy of Intrahepatic Cholangiocarcinomas Revealed by Next-Generation Sequencing, Oncologist, 2014, pp. 235-242, 19(3).

Rubin, B. P., et al., Congenital Mesoblastic Nephroma t(12;15) Is Associated with ETV6-NTRK3 Gene Fusion; Cytogenetic and Molecular Relationship to Congenital (Infantile) Fibrosarcoma, American Journal of Pathology, 1998, pp. 1451-1458, 153(5).

Shan-Rong S et al., Antigen Retrieval Immunohistochemistry: Review and Future Prospects in Research and Diagnosis over Two Decades, J Histochem Cytochem, (2011), pp. 13-32, vol. 59 Issue 1.

Stransky et al., The landscape of kinase fusions in cancer, Nature Communications, 2014, doi: 10.1038/hcomms5846, pp. 1-10, vol. 5, Article No. 4846.

Tognon, C. et al., Expression of the ETV6-NTRK3 gene fusion as a primary event in human secretory breast carcinoma, Cancer Cell, Nov. 2002, pp. 367-376, 2.

Vaishnavi, A. et al., Oncogenic and drug-sensitive NTRK1 rearrangements in lung cancer, Nature Medicine, 2013, pp. 1469-1472, 19(11).

Vinod, K.R. et al., A simple and effective heat induced antigen retrieval method, MethodsX, Apr. 8, 2016, pp. 315-319, vol. 3.

Warford, A. et al, "Antigen retrieval, blocking, detection and visualisation systems in immunohistochemistry: A review and practical evaluation of tyramide and rolling circle amplification systems", Methods, (2014), pp. 28-3, vol. 70.

Wellcome Sanger Institute, COSMIC—the Catalogue of Somatic Mutations in Cancer (COSMIC database), available at http://cancer.sanger.ac.uk/cosmic/fusion, 19 pages (last accessed Sep. 13, 2018).

Yamashita et al., Mechanisms of Heat-induced Antigen Retrieval: Analyses In Vitro Employing SDS-PAGE and Immunohistochemistry, J. Histochemistry and Cytochemistry, 2005, pp. 13-21, vol. 53, Issue 1.

Abcam. "Anti-Pan Trk antibody [EPR17341] ab181560", p. 2, Target. Relevance, 1998-2024, Catalogue.

Feng et al., TRK wild-type and fusion protein expression in solid tumors: Characterization by immunohistochemistry and in situ hybridization, Annals of Oncology, vol. 29, Supp 6, 1 page (abstract), 2018.

Wang, D.P. et al. "Extensive Survey of pan TRK Expression in a Large Series of Sarcomas". Laboratory Investigation, col. 98, suppl. 1, No. 113, Mar. 17, 2018, p. 39, doi.org/10.1038/labinvest.2018.2.

* cited by examiner

```
TrkA    DTNSTSGDPVEKKDETPFGVSVAVGLAVFACLFLSTLLLVLNKCGRRNKFGINRPAVLAP
TrkB    ------------------------------------------------------------
TrkC    ------------------------------------------------------------

TrkA    EDGLAMSLHFMTLGGSSLSPTEGKGSGLQGHIIENPQYFSDACVHHIKRRDIVLKWELGE
TrkB    ------------------------------------------------------------
TrkC    ------------------------------------------------------------

TrkA    GAFGKVFLAECHNLLPEQDKMLVAVKALKEASESARQDFQREAELLTMLQHQHIVRFFGV
TrkB    ------------------------------------------------------------
TrkC    ------------------------------------------------------------

TrkA    CTEGRPLLMVFEYMRHGDLNRFLRSHGPDAKLLAGGEDVAPGPLGLGQLLAVASQVAAGM
TrkB    -----------------------AHGPDAVLMAEGN--PPTELTQSQMLHIAQQIAAGM
TrkC    ------------------------------------------------------------

TrkA    VYLAGLHFVHRDLATRNCLVGQGLVVKIGDFGMSRDIYSTDYYRVGGRTMLPIRWMPPES
TrkB    VYLASQHFVHRDLATRNCLVGENLLVKIGDFGMSRDVYSTDYYRVGGHTMLPIRWMPPES
TrkC    ------------------------------NDFCI--------WCEVGGHTMLPIRWMPPES

TrkA    ILYRKFTTESDVWSFGVVLWEIFTYGKQPWYQLSNTEAIDCITQGRELERPRACPPEVYA
TrkB    IMYRKFTTESDVWSLGVVLWEIFTYGKQPWYQLSNNEVIECITQGRVLQRPRTCPQEVYE
TrkC    IMYRKFTTESDVWSFGVILWEIFTYGKQPWFQLSNTEVIECITQGRVLERPRVCPKEVYD

TrkA    IMRGCWQREPQQRHSIKDVHARLQALAQAPPVYLDVLG (363-760 of SEQ ID NO: 1)
TrkB    LMLGCWQREPHMRKNIKGIHTLLQNLAKASPVYLDILG (646-838 of SEQ ID NO: 2)
TrkC    VMLGCWQREPQQRLNIKEIYKILHALGKATPIYLDILG (718-839 of SEQ ID NO: 3)
```

Fig. 1

HISTOCHEMICAL AND CYTOCHEMICAL METHODS FOR DETECTING NTRK FUSION PROTEINS

CROSS-REFERENCE TO RELATED APPLICATIONS

This application is a continuation of PCT/EP2019/074463, filed Sep. 13, 2019, which claims the benefit of U.S. Provisional Patent Application No. 62/731,032, entitled HISTOCHEMICAL AND CYTOCHEMICAL METHODS FOR DETECTING NTRK FUSION PROTEINS, filed on Sep. 13, 2018, the content of each which is incorporated herein by reference in its entirety.

SEQUENCE LISTING INCORPORATION BY REFERENCE

This application hereby incorporates-by-reference a sequence listing submitted herewith in a computer-readable format, having a file name of "P35023US1_SeqList_ST25" created on Feb. 1, 2021, which is 21,275 bytes in size.

TECHNICAL FIELD

The present disclosure relates, among other things, to methods for the histochemical and cytochemical detection of fusion proteins involving NTRK gene products; materials, kits, and systems useful in such methods; and products resulting from performance of such methods.

BACKGROUND

Neurotrophic tyrosine receptor kinases (NTRK1, NTRK2, and NTRK3) are a gene family encoding receptor tyrosine kinase proteins (TRKA, TRKB and TRKC) which play a role in the development and maturation of the central and peripheral nervous systems (Barbacid I, Barbacid II, Lemmon & Schlessinger, and Klein). In cancer, the intact kinase domain of one of the three NTRK genes can fuse to a variety of upstream partners (e.g. ETV6, LMNA, TPM3) replacing the TRK protein's ligand binding domain with structural motifs promoting dimerization (Eide, Luberg, & Vaishnavi). This results in constitutive activation of TRK signaling and unchecked proliferation, resulting from expression of the fusion protein.

NTRK gene fusions are pathognomonic in certain rare tumors such as infantile fibrosarcoma, congenital mesoblastic nephroma, secretory breast cancer and secretory carcinoma (MASC) of the salivary gland (Argani, Bishop, Bourgeois, Rubin, & Tognon). Conversely, NTRK gene fusions occur rarely in a variety of adult and pediatric solid tumors, including but not limited to: appendiceal cancer, breast cancer, cholangiocarcinoma, colorectal cancer (CRC), GIST, lung cancer, melanoma, pancreatic cancer, thyroid cancer, and diverse sarcomas (DeBraud, Brzezianska, Fernandez-Cuesta, Leeman-Neill, & Ross). Identifying NTRK gene fusions is clinically important because of the availability of small molecule inhibitors currently in development for the treatment of solid tumors with NTRK gene fusions (Vaishnavi & De Braud).

To date, there is no gold standard for detection of NTRK fusions in tumors due to inconsistent specificity and sensitivity across different methodologies. Current methods of detection include fluorescence in situ hybridization (FISH), in situ hybridization (ISH), Next Generation Sequencing (NGS), and immunohistochemistry (IHC). Optimization and enumeration/interpretation of FISH and ISH assays can be difficult. NGS is highly specific, but lacks sensitivity. In contrast, IHC can be highly sensitive, but detects protein expression rather than the presence of actual fusion. Additionally, due to endogenous presence of wild-type TRK protein in some tumors (namely neuroendocrine tumors and GISTs), optimization of an IHC assay to the fusion product, and in turn, development of a specific scoring algorithm to select for this fusion product, can be challenging.

SUMMARY

The present disclosure relates to methods for identifying non-neuroendocrine tumors that are driven by TRK fusion proteins.

In an embodiment, a method of detecting a fusion protein of TrkA, TrkB, or TrkC in a non-neuroendocrine tumor sample is provided, the method comprising: affinity histochemically staining the sample with a biomarker-specific reagent that specifically binds to one or more of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3; detecting staining pattern in the sample; and scoring the sample as positive for a fusion protein involving TrkA, TrkB, or TrkC if: the sample has a cytoplasmic and/or membranous staining pattern and has a greater than or equal to a first threshold percentage of tumor cells staining above a pre-determined specific staining intensity; or the sample has a nuclear staining pattern and greater than or equal to a second threshold percentage of cells within a threshold tumor cell area that are specifically stained at any intensity.

In an embodiment, a method of detecting a fusion protein of TrkA, TrkB, or TrkC in a non-neuroendocrine tumor sample is provided, the method comprising: affinity histochemically staining the sample with a biomarker-specific reagent that specifically binds to: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; and an amino acid sequence comprising, consisting essentially of, or consisting of residues 718-839 of SEQ ID NO: 3; detecting staining pattern in the sample; and scoring the sample as positive for a fusion protein involving TrkA, TrkB, or TrkC if: the sample has a cytoplasmic and/or membranous staining pattern and has a greater than or equal to a first threshold percentage of tumor cells staining above a pre-determined specific staining intensity; or the sample has a nuclear staining pattern and greater than or equal to a second threshold percentage of cells within a threshold tumor cell area that are specifically stained at any intensity.

In an embodiment, a method of detecting a fusion protein of TrkA, TrkB, or TrkC in a non-neuroendocrine tumor sample is provided, the method comprising: affinity histochemically staining the sample with a biomarker-specific reagent that specifically binds to an amino acid sequence consisting of amino acids 816-838 of SEQ ID NO: 2; detecting staining pattern in the sample; and scoring the sample as positive for a fusion protein involving TrkA, TrkB, or TrkC if: the sample has a cytoplasmic and/or membranous staining pattern and has a greater than or equal to a first threshold percentage of tumor cells staining above a pre-determined specific staining intensity; or the sample has a nuclear staining pattern and greater than or equal to a second threshold percentage of cells within a threshold tumor cell area that are specifically stained at any intensity.

In an embodiment, a method of detecting an NTRK rearrangement in a non-neuroendocrine tumor sample is provided, the method comprising detecting the presence of a Trk fusion protein in the sample according to a method described herein, and confirming the presence of an NTRK rearrangement by screening the sample by sequencing, reverse transcriptase polymerase chain reaction, or in situ hybridization if the sample is scored as positive for a fusion protein involving TrkA, TrkB, or TrkC.

In an embodiment, a method of selecting a patient to receive a Trk-directed therapy is provided, the method comprising detecting the presence of a Trk fusion protein or an NTRK rearrangement in a non-neuroendocrine tumor sample according to a method described herein, and selecting the patient to receive the therapy if the sample is scored as positive for a fusion protein involving TrkA, TrkB, or TrkC or the NTRK rearrangement is detected.

In an embodiment, methods of staining samples for the presence or absence of TrkA, TrkB, or TrkC, and fusion proteins involving the kinase domain thereof, are also provided, the methods comprising (a) subjecting the sample to a heat-induced epitope retrieval process; and (b) contacting the sample with the biomarker-specific reagent and a set of detection reagents to deposit a brightfield dye in proximity to any biomarker-specific reagent bound to the sample, wherein the biomarker-specific reagent specifically binds to one or more of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3.

In an embodiment, methods of staining samples for the presence or absence of TrkA, TrkB, or TrkC, and fusion proteins involving the kinase domain thereof, are also provided, the methods comprising (a) subjecting the sample to a heat-induced epitope retrieval process; and (b) contacting the sample with the biomarker-specific reagent and a set of detection reagents to deposit a brightfield dye in proximity to any biomarker-specific reagent bound to the sample, wherein the biomarker-specific reagent is a primary antibody that specifically binds to one or more of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3; and wherein the set of detection reagents comprises a secondary antibody immunoreactive with the primary antibody, a tertiary antibody immunoreactive with the secondary antibody conjugated to an enzyme, and a set of reagents reactive with the enzyme to effect deposition of a brightfield dye on the sample.

In an embodiment, methods of staining samples for the presence or absence of TrkA, TrkB, or TrkC, and fusion proteins involving the kinase domain thereof, are also provided, the methods comprising (a) subjecting the sample to a heat-induced epitope retrieval process; and (b) contacting the sample with the biomarker-specific reagent and a set of detection reagents to deposit a brightfield dye in proximity to any biomarker-specific reagent bound to the sample, wherein the biomarker-specific reagent is a primary antibody that specifically binds to each of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3; and wherein the set of detection reagents comprises a secondary antibody immunoreactive with the primary antibody, a tertiary antibody immunoreactive with the secondary antibody conjugated to an enzyme, and a set of reagents reactive with the enzyme to effect deposition of a brightfield dye on the sample. Other embodiments will be apparent from the following disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 Sequence alignment between exemplary retained portions of TrkA (amino acid residues 363-760 of SEQ ID NO: 1), TrkB (amino acid residues 646-838 of SEQ ID NO: 2) and TrkC (amino acid residues 718-839 of SEQ ID NO: 3). The sequence alignment was generated using the Kalign Multiple Sequence Alignment tool from EMBL-EBI (https://www.ebi.ac.uk/Tools/msa/kalign/). Default settings were used, which include a ClustalW output format, a Gap Open Penalty of 11, a Gap Extension Penalty of 0.85, Terminal Gap Penalties of 0.45, and Bonus Score of 0.

FIG. 5a shows and FIG. 5b shows staining distribution of neuroendocrine tumors where no fusion-positive cases were detected.

DETAILED DESCRIPTION

I. Definitions

Figure 2A:
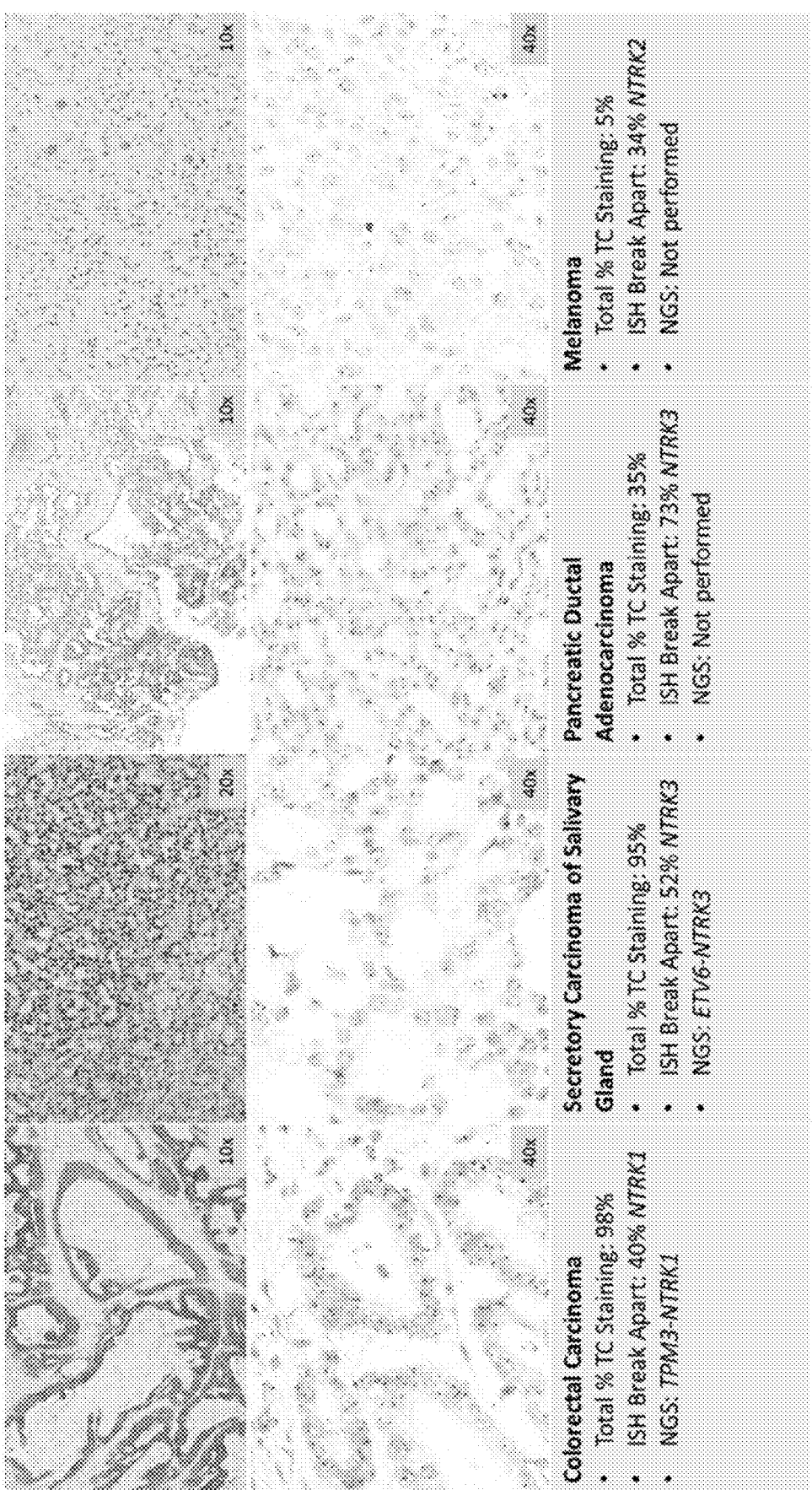
FIG. 2A IHC results for Trk-fusions in multiple tumor types. Orthogonal testing methods were used to assess for presence of Trk fusions.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is:

characteristic of a particular cell or tissue type or state;

characteristic of a particular pathological condition or state; or indicative of the severity of a pathological condition, the likelihood of progression or regression of the pathological condition, and/or the likelihood that the pathological condition will respond to a particular treatment.

As another example, the biomarker may be a cell type or a microorganism (such as a bacteria, mycobacteria, fungi, viruses, and the like), or a substituent molecule or group of molecules thereof.

Biomarker-specific reagent: A specific detection reagent that is capable of specifically binding directly to one or more biomarkers in the cellular sample, such as a primary antibody.

Cellular sample: As used herein, the term "cellular sample" refers to any sample containing intact cells, such as cell cultures, bodily fluid samples or surgical specimens taken for pathological, histological, or cytological interpretation.

Cytochemical detection: A process involving labelling biomarkers or other structures in a cytological sample with biomarker-specific reagents and detection reagents in a manner that permits microscopic detection of the biomarker or other structures in the context of intact cells.

Cytological sample: As used herein, the term "cytological sample" shall refer to a cellular sample that either have no cross-sectional spatial relationship in vivo (such as cellular samples derived from blood samples, urine samples, sputum, etc.) or in which the cross-sectional spatial relationship has been at least partially disrupted (such as tissue smears, liquid-based cytology samples, fine needle aspirates, etc.).

Detection reagent: A "detection reagent" is any reagent that is used to deposit a stain in proximity to a biomarker-specific reagent in a cellular sample. Non-limiting examples include biomarker-specific reagents (such as primary antibodies), secondary detection reagents (such as secondary antibodies capable of binding to a primary antibody), tertiary detection reagents (such as tertiary antibodies capable of binding to secondary antibodies), enzymes directly or indirectly associated with the biomarker specific reagent, chemicals reactive with such enzymes to effect deposition of a fluorescent or chromogenic stain, wash reagents used between staining steps, and the like.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultraviolet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, 11th Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

Histochemical detection: A process involving labelling biomarkers or other structures in a tissue sample with biomarker-specific reagents and detection reagents in a manner that permits microscopic detection of the biomarker or other structures in the context of the cross-sectional relationship between the structures of the tissue sample.

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

"Retained portion" shall mean any portion of a wild-type counterpart of an oncogenic fusion protein that is preserved in the oncogenic fusion protein.

Specific binding: As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of $\leq 1$ µM, $\leq 100$ nM, $\leq 10$ nM, $\leq 1$ nM, or $\leq 0.1$ nM. In another embodiment, specific binding can include, but does not require exclusive binding.

Specific detection reagent: Any composition of matter that is capable of specifically binding to a target chemical structure in the context of a cellular sample.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

Test sample: A tumor sample obtained from a subject having an unknown outcome at the time the sample is obtained.

Tissue sample: As used herein, the term "tissue sample" shall refer to a cellular sample that preserves the cross-sectional spatial relationship between the cells as they existed within the subject from which the sample was obtained.

Tumor sample: A tissue sample obtained from a tumor.

II. Staining Methods

The disclosure is based on affinity histochemically or cytochemically-stained samples of non-neuroendocrine NTRK fusion proteins using a first biomarker specific reagent that targets a retained portion of one or more of TrkA, TrkB, and TrkC. The biomarker-specific reagent is selected by identifying the breakpoint of the wild-type protein that results in the fusion protein, and targeting a portion of the wild-type protein on the side of the breakpoint retained in the fusion protein. Many resources are available for identifying fusion protein breakpoints including, for example, the COSMIC database, which includes notations of breakpoints by genomic location and by the first exon expressed in the resulting fusion protein. Exemplary wild-type protein sequences are set forth in Table 1:

TABLE 1

| Wild-type protein | Exemplary amino acid sequence | Background References |
|---|---|---|
| TrkA | Uniprot P04629-3 (SEQ ID NO: 1) | Amatu et al.; Stransky et al. |
| TrkB | Uniprot Q16620-4 (SEQ ID NO: 2) | Amatu et al.; Stransky et al. |
| TrkC | Uniprot Q16288-1 (SEQ ID NO: 3) | Amatu et al.; Stransky et al. |

Exemplary breakpoints and consensus retained portions for fusion proteins retaining the C-terminus of TrkA, TrkB, or TrkC are illustrated in Table 2:

TABLE 2

| Wild-type protein | Fusion Partner | First Observed Exon | Consensus Retained Portion |
|---|---|---|---|
| TrkA | LMNA | 10‡ | Exon 10 through C-terminus |
|  | TFG | 6‡ | (Residues 363-760 of |
|  | TP53 | 9‡ | SEQ ID NO: 1) |
|  | TPM3 | 10‡ |  |
| TrkB | AFAP1 | 12* | Exon 17 through C-terminus |
|  | NACC2 | 13‡ | (Residues 646-838 of |
|  | QKI | 16‡ | SEQ ID NO: 2) |
|  | PAN3 | 17* |  |
|  | SQSTM | 16 (terminates at exon 20)* |  |
|  | TRIM24 | 15* |  |
| TrkC | ETV6 | 15‡ | Exon 15 through C-terminus |
|  |  | 14‡ | (Residues 718-839 of |
|  | TECR | 10* | SEQ ID NO: 3) |

In an embodiment, the biomarker-specific reagent specifically binds to a retained portion of one or more of TrkA, TrkB, and TrkC. In an embodiment, the biomarker-specific reagent specifically binds to a retained portion of each of TrkA, TrkB, and TrkC. An alignment between exemplary retained portions of TrkA, TrkB, and TrkC is illustrated at FIG. 1. In another specific embodiment, the biomarker-specific reagent specifically binds to one or more of: (a) an amino acid sequence comprising, consisting essentially of, or consisting of residues 363-760 of SEQ ID NO: 1; (b) an amino acid sequence comprising, consisting essentially of, or consisting of residues 646-838 of SEQ ID NO: 2; or (c) an amino acid sequence comprising, consisting essentially of, or consisting of residues 718-839 of SEQ ID NO: 3. In another specific embodiment, the biomarker-specific reagent specifically binds to: (a) an amino acid sequence comprising, consisting essentially of, or consisting of residues 363-760 of SEQ ID NO: 1; (b) an amino acid sequence comprising, consisting essentially of, or consisting of residues 646-838 of SEQ ID NO: 2; and (c) an amino acid sequence comprising, consisting essentially of, or consisting of residues 718-839 of SEQ ID NO: 3.

The biomarker-specific reagent may be any type of entity that is useful for in situ detection of proteins expressed by a cellular sample (such as by in histological or cytological staining methods). Exemplary biomarker-specific reagents include antibodies and antigen binding fragments thereof and engineered specific binding compositions, such as ADNECTINs (scaffold based on 10th FN3 fibronectin; Bristol-Myers-Squibb Co.), AFFIBODYs (scaffold based on Z domain of protein A from *S. aureus*; Affibody AB, Solna, Sweden), AVIMERs (scaffold based on domain A/LDL receptor; Amgen, Thousand Oaks, CA), dAbs (scaffold based on VH or VL antibody domain; GlaxoSmithKline PLC, Cambridge, UK), DARPins (scaffold based on Ankyrin repeat proteins; Molecular Partners AG, Zürich, CH), ANTICALINs (scaffold based on lipocalins; Pieris A G, Freising, DE), NANOBODYs (scaffold based on VHH (camelid Ig); Ablynx N/V, Ghent, BE), TRANS-BODYs (scaffold based on Transferrin; Pfizer Inc., New York, NY), SMIPs (Emergent Biosolutions, Inc., Rockville, MD), and TETRANECTINs (scaffold based on C-type lectin domain (CTLD), tetranectin; Borean Pharma A/S, Aarhus, D K). Descriptions of such engineered specific binding structures are reviewed by Wurch et al., Development of Novel Protein Scaffolds as Alternatives to Whole Antibodies for Imaging and Therapy: Status on Discovery Research and Clinical Validation, Current Pharmaceutical Biotechnology, Vol. 9, pp. 502-509 (2008), the content of which is incorporated by reference.

In a specific embodiment, the biomarker-specific reagent is an antibody. In another specific embodiment, the antibody is a monoclonal antibody (such as mouse monoclonal or rabbit monoclonal antibodies). In another specific embodiment, the antibody specifically binds to a retained portion of one or more of TrkA, TrkB, or TrkC. In another specific embodiment, the antibody specifically binds to an epitope contained in one or more of: (a) an amino acid sequence comprising, consisting essentially of, or consisting of residues 363-760 of SEQ ID NO: 1; (b) an amino acid sequence comprising, consisting essentially of, or consisting of residues 646-838 of SEQ ID NO: 2; or (c) an amino acid sequence comprising, consisting essentially of, or consisting of residues 718-839 of SEQ ID NO: 3. In another specific embodiment, the antibody specifically binds to: (a) an amino acid sequence comprising, consisting essentially of, or consisting of residues 363-760 of SEQ ID NO: 1; (b) an amino acid sequence comprising, consisting essentially of, or consisting of residues 646-838 of SEQ ID NO: 2; and (c) an amino acid sequence comprising, consisting essentially of, or consisting of residues 718-839 of SEQ ID NO: 3. In an embodiment, the antibody is a commercially available antibody according to Table 3:

TABLE 3

| EPR17341 | Abcam (ab181560) | Rabbit monoclonal IgG | 816-838 of SEQ ID NO: 2 |
|---|---|---|---|
| B-3 | Santa Cruz Biotechnology Inc. (sc-7268) | Mouse monoclonal IgG2a | 747-760 of SEQ ID NO: 1 |

In a specific embodiment, the antibody is EPR17341.

The biomarker-specific reagent is used to affinity histochemically or affinity cytochemically stain samples suspected of harboring a NTRK fusion protein. Affinity histochemical and cytochemical staining techniques typically involve contacting a sample deposited on a slide or other solid support with a biomarker-specific reagent under conditions sufficient to permit specific binding between the biomarker-specific reagent and the biomarker of interest. Binding of the biomarker-specific reagent to the biomarker facilitates deposition of a detectable moiety on the sample in proximity to locations containing the biomarker. The detectable moiety can be used to locate and/or quantify the biomarker to which the biomarker-specific reagent is directed. Thereby, the presence and/or relative amount of the target in a sample can be detected by detecting the signal produced by the detectable moiety.

The staining process may be manual, automated, or a combination of manual and automated steps. In an embodiment, the staining process may be carried out on an automated advanced staining platform. Automated advanced staining platforms typically include at least: reservoirs of the various reagents used in the staining protocols, a reagent dispense unit in fluid communication with the reservoirs for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), epitope retrieval, counterstaining, dehydration and clearing, and coverslipping. Prichard describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be used.

The staining methods are practiced on cellular samples of the suspected tissue, including tissue samples and cytological samples. In some embodiments, the cellular sample is obtained from a subject having or suspected of having a tumor. In some embodiments, the sample is obtained directly from a tumor. In some embodiments, the tumor is a solid tumor, such as a carcinoma, lymphoma, or sarcoma. In an embodiment, the tumor is a non-neuroendocrine tumor. In an embodiment, the non-neuroendocrine tumor is a solid tumor of the salivary gland, thyroid, skin, breast, head and/or neck, lung, upper gastrointestinal tract (including the esophagus and stomach), female reproductive system (including uterine, fallopian, and ovarian tumors), lower gastrointestinal tract (including the colon, rectal, and anal tumors), urogenital tract, exocrine, endocrine, renal, or of lymphocytic origin. In an embodiment, subject has a melanoma, salivary cancer, thyroid cancer, breast cancer, ovarian cancer, pancreatic cancer, head and neck cancer, lung cancer, esophageal cancer, gastric cancer (excluding gastrointestinal stromal tumors (GIST)), colorectal cancer (including cancer of the colon, rectum, and anus), prostate cancer, urothelial cancer, or lymphoma.

Where tissue samples are used, the tissue sample is processed in a manner compatible with histochemical staining, including, for example, fixation, embedding in a wax matrix (such as paraffin), and sectioning (such as with a microtome). No specific processing step is required by the present disclosure, so long as the sample obtained is compatible with histochemical staining of the sample with the set of biomarker-specific reagents. In a specific embodiment, microtome sections of formalin-fixed, paraffin-embedded (FFPE) samples are used in the staining process. Where cytological samples are used, the sample is fixed in formalin.

Depending on the biomarker-specific reagent being used and the sample being used, the sample may be subjected to an epitope retrieval process (also referred to as antigen retrieval) prior to application of the biomarker-specific reagent. Exemplary epitope retrieval processes include: heat-induced epitope retrieval (HIER), which involves heating the sample in various buffers at different pH levels; protease-based epitope retrieval (PBER), in which samples are digested by proteolytic enzymes prior to staining; and combinations of HIER and PBER. Various specific epitope retrieval processes are reviewed by Shi et al., D'Amico et al., Yamashita et al., Vinod et al., and Warford et al., although this is not exhaustive. Whether to perform epitope retrieval and the particular form of epitope retrieval to use depends on the specific biomarker-specific reagent selected, and may need to be empirically determined for each biomarker-specific reagent used.

Depending on the reagents and samples used, it may also be desirable to block activity of endogenous proteins prior to addition of biomarker-specific reagents and/or detection reagents. For example, where the detection reagents depend on biotin and biotin-binding proteins, it may be necessary to block endogenous biotin using, for example, free, unlabeled biotin-binding proteins. Likewise, many detection schemes rely on activity of enzymes, including phosphatases and peroxidases, which necessitates neutralization of endogenous enzymes having similar activities. Commercially-available kits are available for such blocking processes, e.g., Endogenous Biotin Blocking Kit (Cat. No. E21390, ThermoFisher Scientific), Endogenous Avidin/Biotin Blocking Kit (Cat. No. ab64212, Abcam, plc.), Endogenous Biotin Blocking Kit Cat. No. 760-050, Ventana Medical Systems, Inc.), Hydrogen Peroxide Blocking Reagent (Cat. No. ab64218, Abcam plc.), Peroxidase and Alkaline Phosphatase Blocking Reagent, (Code S2003, Agilent Technologies), among others.

It may also be useful to block sites on the sample to which the biomarker-specific reagent may bind non-specifically before applying the biomarker-specific reagent to the sample. Common blocking agents include buffered solutions of normal serum, non-fat dry milk, BSA (bovine serum albumin), and gelatin, as well as commercially available blocking agents such as eBioscience™ IHC/ICC Blocking Buffer-High Protein (Cat. No. 00-4952-54, ThermoFisher Scientific), eBioscience™ IHC/ICC Blocking Buffer-Low Protein (Cat. No. 00-4953-54, ThermoFisher Scientific), DISCOVERY antibody Block (Cat. No. 760-4204, Ventana Medical Systems, Inc.), among others.

Washing steps may be performed after each of these pre-processing steps by applying one or more passes of a wash buffer. Wash buffers typically are neutrally-buffered saline solutions, which may also contain small amounts of detergent. Exemplary wash buffers include, for example, Phosphate Buffered Saline (PBS), PBS-Tween20, Tris Buffered Saline (TBS), TBS-Tween20 (polysorbate 20), Tris-HCl, Tris-HC-Tween20, Phosphate Buffer (PB), AP Buffer, and the like.

Once the sample has been prepared for staining, the biomarker-specific reagent is applied to the sample and incubated for a sufficient period of time and under conditions to promote specific binding between the biomarker and the biomarker-specific reagent. A washing step may be performed after the sample is incubated with the biomarker-specific reagent by applying one or more passes of a wash buffer. This removes unbound or non-specifically bound biomarker-specific reagent from the sample to mitigate off-target and/or background staining.

Detection of the biomarker in the sample is achieved by depositing a detectable moiety in close proximity to the biomarker-specific reagent bound to the sample. In some embodiments, the detectable moiety is directly conjugated to the biomarker-specific reagent, and thus is deposited on the sample upon binding of the biomarker-specific reagent to its target (generally referred to as a direct labeling method). In other embodiments, deposition of the detectable moiety is effected by the applying a set of detection reagents to the sample after the application of the biomarker-specific reagent, wherein the detection reagents bind to or otherwise react with the biomarker-specific reagent in a manner the effects deposition of the detectable moiety (generally referred to as an indirect labeling method).

In some embodiments in which an indirect method is used, the detectable moiety is deposited via an enzymatic reaction localized to the biomarker-specific reagent. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:

(a) a specific detection reagent; and (b) an enzyme conjugated to the specific detection reagent, wherein the enzyme is reactive with a chromogenic substrate, a signaling conjugate, and/or an enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate] (ABTS), o-dianisidine, 4-chloronaphthol (4—CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxidoreductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indodicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of biomarker-specific reagent and detection reagent combinations are set forth in Table 4 are specifically included.

TABLE 4

| A. Biomarker-specific reagent linked directly to detectable moiety |
| --- |
| Biomarker-specific reagent-Dye conjugate |
| B. Biomarker-specific reagent linked to enzyme reacting with detectable moiety |
| Biomarker-specific reagent-Enzyme conjugate + DAB |
| Biomarker-specific reagent-Enzyme conjugate + Chromogen |
| Biomarker-specific reagent-Enzyme conjugate + Fluorophore |

TABLE 4-continued

| C. Biomarker-specific reagent linked to Enzyme reacting with detectable moiety | |
|---|---|
| C1. Signaling conjugate comprises detectable moiety | Biomarker-specific reagent-Enzyme conjugate + QM-Dye conjugate |
| | Biomarker-specific reagent-Enzyme conjugate + Tyramide-Dye conjugate |
| C2. Signaling conjugate comprises enzyme that reacts directly with detectable moiety | Biomarker-specific reagent-Enzyme conjugate + QM-Enzyme conjugate + DAB |
| | Biomarker-specific reagent-Enzyme conjugate + QM-Enzyme conjugate + Chromogen |
| | Biomarker-specific reagent-Enzyme conjugate + QM-Enzyme conjugate + Fluorophore |
| | Biomarker-specific reagent-Enzyme conjugate + Tyramide-Enzyme conjugate + DAB |
| | Biomarker-specific reagent-Enzyme conjugate + Tyramide-Enzyme conjugate + Chromogen |
| | Biomarker-specific reagent-Enzyme conjugate + Tyramide-Enzyme conjugate + Fluorophore |
| C3. Signaling conjugate comprises enzyme that reacts with second signaling conjugate comprising detectable moiety | Biomarker-specific reagent-Enzyme conjugate + QM-Enzyme conjugate + QM-Dye conjugate |
| | Biomarker-specific reagent-Enzyme conjugate + QM-Enzyme conjugate + Tyramide-Dye conjugate |
| | Biomarker-specific reagent-Enzyme conjugate + Tyramide-Enzyme conjugate + QM-Dye conjugate |
| | Biomarker-specific reagent-Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent-Enzyme conjugate + Tyramide-(biotin or hapten) conjugate + Dye-(avidin or anti-hapten specific detection reagent) conjugate |
| | Biomarker-specific reagent-Enzyme conjugate + QM-(biotin or hapten) conjugate + Dye-(avidin or anti-hapten specific detection reagent) conjugate |
| C5. Signaling conjugate comprises member of a specific binding pair and other member of binding pair is linked to enzyme reactive with detectable moiety | Biomarker-specific reagent-Enzyme conjugate + QM-(biotin or hapten) conjugate + Enzyme-(avidin or anti-hapten specific detection reagent) conjugate + DAB |
| | Biomarker-specific reagent-Enzyme conjugate + QM-(biotin or hapten) conjugate + Enzyme-(avidin or anti-hapten specific detection reagent) conjugate + Chromogen |
| | Biomarker-specific reagent-Enzyme conjugate + QM-(biotin or hapten) conjugate + Enzyme-(avidin or anti-hapten specific detection reagent) conjugate + Fluorophore |
| | Biomarker-specific reagent-Enzyme conjugate + Tyramide-(biotin or hapten) conjugate + Enzyme-(avidin or anti-hapten specific detection reagent) conjugate + DAB |
| | Biomarker-specific reagent-Enzyme conjugate + Tyramide-(biotin or hapten) conjugate + Enzyme-(avidin or anti-hapten specific detection reagent) conjugate + Chromogen |
| | Biomarker-specific reagent-Enzyme conjugate + Tyramide-(biotin or hapten) conjugate + Enzyme-(avidin or anti-hapten specific detection reagent) conjugate + Fluorophore |
| C6. Signaling conjugate comprises member of a specific binding pair and other member of binding pair is linked to enzyme reactive with second detectable moiety linked to a detectable moiety | Biomarker-specific reagent-Enzyme conjugate + QM-(biotin or hapten) conjugate + Enzyme-(avidin or anti-hapten specific detection reagent) conjugate + Tyramide-Dye conjugate |
| | Biomarker-specific reagent-Enzyme conjugate + QM-(biotin or hapten) conjugate + Enzyme-(avidin or anti-hapten specific detection reagent) conjugate + QM-Dye conjugate |
| | Biomarker-specific reagent-Enzyme conjugate + Tyramide-(biotin or hapten) conjugate + Enzyme-(avidin or anti-hapten specific detection reagent) conjugate + Tyramide-Dye conjugate |
| | Biomarker-specific reagent-Enzyme conjugate + Tyramide-(biotin or hapten) conjugate + Enzyme-(avidin or anti-hapten specific detection reagent) conjugate + QM-Dye conjugate |
| D. Biomarker-specific reagent linked to member of specific binding pair | |
| D1. Dye linked to other member of specific binding pair | Biomarker-specific reagent-(biotin or hapten) conjugate + Dye-(avidin or anti-hapten specific detection reagent) conjugate |
| D2. Enzyme linked to other member of specific binding pair, wherein the enzyme is reactive with detectable moiety | Biomarker-specific reagent-(biotin or hapten) conjugate + Enzyme-(avidin or anti-hapten specific detection reagent) conjugate + DAB |
| | Biomarker-specific reagent-(biotin or hapten) conjugate + Enzyme-(avidin or anti-hapten specific detection reagent) conjugate + Chromogen |
| | Biomarker-specific reagent-(biotin or hapten) conjugate + Enzyme-(avidin or anti-hapten specific detection reagent) conjugate + fluorophore |

TABLE 4-continued

Biomarker-specific reagent-(biotin or hapten) conjugate +
Enzyme-(avidin or anti-hapten specific detection reagent)
conjugate + QM-Dye conjugate
Biomarker-specific reagent-(biotin or hapten) conjugate +
Enzyme-(avidin or anti-hapten specific detection reagent)
conjugate + Tyramide-Dye conjugate
E. Secondary detection reagent linked directly to detectable moiety Biomarker-specific reagent + 2° specific detection reagent-Dye conjugate
F. Secondary detection reagent linked to Enzyme reacting with detectable moiety Biomarker-specific reagent + 2° specific detection reagent-Enzyme conjugate + DAB
Biomarker-specific reagent + 2° specific detection reagent-Enzyme conjugate + Chromogen
Biomarker-specific reagent + 2° specific detection reagent-Enzyme conjugate + Fluorophore
G. Secondary detection reagent linked to Enzyme reacting with detectable moiety

| | |
|---|---|
| G1. Signaling conjugate comprises detectable moiety | Biomarker-specific reagent + 2° specific detection reagent-Enzyme conjugate + QM-Dye conjugate<br>Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB<br>Biomarker-specific reagent + 2° specific detection reagent-Enzyme conjugate + QM-Enzyme conjugate + Chromogen<br>Biomarker-specific reagent + 2° specific detection reagent-Enzyme conjugate + QM-Enzyme conjugate + Fluorophore<br>Biomarker-specific reagent + 2° specific detection reagent-Enzyme conjugate + Tyramide-Enzyme conjugate + DAB<br>Biomarker-specific reagent + 2° specific detection reagent-Enzyme conjugate + Tyramide-Enzyme conjugate + Chromogen<br>Biomarker-specific reagent + 2° specific detection reagent-Enzyme conjugate + Tyramide-Enzyme conjugate + Fluorophore |
| G3. Signaling conjugate comprises enzyme that reacts with second signaling conjugate comprising detectable moiety | Biomarker-specific reagent + 2° specific detection reagent-Enzyme conjugate + QM-Enzyme conjugate + QM-Dye conjugate<br>Biomarker-specific reagent + 2° specific detection reagent-Enzyme conjugate + QM-Enzyme conjugate + Tyramide-Dye conjugate<br>Biomarker-specific reagent + 2° specific detection reagent-Enzyme conjugate + Tyramide-Enzyme conjugate + QM-Dye conjugate<br>Biomarker-specific reagent + 2° specific detection reagent-Enzyme conjugate + Tyramide-Enzyme conjugate + Tyramide-Dye conjugate |
| G4. Signaling conjugate comprises member of a specific binding pair and other member of binding pair is linked to detectable moiety | Biomarker-specific reagent + 2° specific detection reagent-Enzyme conjugate + Tyramide-(biotin or hapten) conjugate + Dye-(avidin or anti-hapten specific detection reagent) conjugate<br>Biomarker-specific reagent + 2° specific detection reagent-Enzyme conjugate + QM-(biotin or hapten) conjugate + Dye-(avidin or anti-hapten specific detection reagent) conjugate |
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin or hapten) conjugate + Enzyme-(avidin or anti-hapten specific detection reagent) conjugate + DAB<br>Biomarker-specific reagent + 2° specific detection reagent-Enzyme conjugate + QM-(biotin or hapten) conjugate + Enzyme-(avidin or anti-hapten specific detection reagent) conjugate + Chromogen<br>Biomarker-specific reagent + 2° specific detection reagent-Enzyme conjugate + QM-(biotin or hapten) conjugate + Enzyme-(avidin or anti-hapten specific detection reagent) conjugate + Fluorophore<br>Biomarker-specific reagent + 2° specific detection reagent-Enzyme conjugate + Tyramide-(biotin or hapten) conjugate + Enzyme-(avidin or anti-hapten specific detection reagent) conjugate + DAB<br>Biomarker-specific reagent + 2° specific detection reagent-Enzyme conjugate + Tyramide-(biotin or hapten) conjugate + Enzyme-(avidin or anti-hapten specific detection reagent) conjugate + Chromogen<br>Biomarker-specific reagent + 2° specific detection reagent-Enzyme conjugate + Tyramide-(biotin or hapten) conjugate + Enzyme-(avidin or anti-hapten specific detection reagent) conjugate + Flurophore |

TABLE 4-continued

| | |
|---|---|
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin or hapten) conjugate + Enzyme-(avidin or anti-hapten specific detection reagent) conjugate + Tyramide-Dye conjugate<br>Biomarker-specific reagent + 2° specific detection reagent-Enzyme conjugate + QM-(biotin or hapten) conjugate + Enzyme-(avidin or anti-hapten specific detection reagent) conjugate + QM-Dye conjugate<br>Biomarker-specific reagent + 2° specific detection reagent-Enzyme conjugate + Tyramide-(biotin or hapten) conjugate + Enzyme-(avidin or anti-hapten specific detection reagent) conjugate + Tyramide-Dye conjugate<br>Biomarker-specific reagent + 2° specific detection reagent-Enzyme conjugate + Tyramide-(biotin or hapten) conjugate + Enzyme-(avidin or anti-hapten specific detection reagent) conjugate + QM-Dye conjugate |

H. Secondary detection reagent linked to member of specific binding pair

| | |
|---|---|
| H1. Dye linked to other member of specific binding pair | Biomarker-specific reagent + 2° specific detection reagent-(biotin or hapten) conjugate + Dye-(avidin or anti-hapten specific detection reagent) conjugate |
| H2. Enzyme linked to other member of specific binding pair, wherein the enzyme is reactive with detectable moiety | Biomarker-specific reagent + 2° specific detection reagent-(biotin or hapten) conjugate + Enzyme-(avidin or anti-hapten specific detection reagent) conjugate + DAB<br>Biomarker-specific reagent + 2° specific detection reagent-(biotin or hapten) conjugate + Enzyme-(avidin or anti-hapten specific detection reagent) conjugate + Chromogen<br>Biomarker-specific reagent + 2° specific detection reagent-(biotin or hapten) conjugate + Enzyme-(avidin or anti-hapten specific detection reagent) conjugate + Fluorophore<br>Biomarker-specific reagent + 2° specific detection reagent-(biotin or hapten) conjugate + Enzyme-(avidin or anti-hapten specific detection reagent) conjugate + QM-Dye conjugate<br>Biomarker-specific reagent + 2° specific detection reagent-(biotin or hapten) conjugate + Enzyme-(avidin or anti-hapten specific detection reagent) conjugate + Tyramide-Dye conjugate |

I. Tertiary specific detection reagent linked directly to detectable moiety

Biomarker-specific reagent + 2° specific detection reagent +
3° specific detection reagent-Dye conjugate J. Tertiary specific detection reagent linked to Enzyme reacting with detectable moiety Biomarker-specific reagent + 2° specific detection reagent +
3° specific detection reagent-Enzyme conjugate + DAB
Biomarker-specific reagent + 2° specific detection reagent +
3° specific detection reagent-Enzyme conjugate + Chromogen
Biomarker-specific reagent + 2° specific detection reagent +
3° specific detection reagent-Enzyme conjugate + Fluorophore K. Tertiary specific detection reagent linked to Enzyme reacting with detectable moiety

| | |
|---|---|
| K1. Signaling conjugate comprises detectable moiety | Biomarker-specific reagent + 2° specific detection reagent + 3° specific detection reagent-Enzyme conjugate + QM-Dye conjugate<br>Biomarker-specific reagent + 2° specific detection reagent + 3° specific detection reagent-Enzyme conjugate + Tyramide-Dye conjugate |
| K2. Signaling conjugate comprises enzyme that reacts directly with detectable moiety | Biomarker-specific reagent + 2° specific detection reagent + 3° specific detection reagent-Enzyme conjugate + QM-Enzyme conjugate + DAB<br>Biomarker-specific reagent + 2° specific detection reagent + 3° specific detection reagent-Enzyme conjugate + QM-Enzyme conjugate + Chromogen<br>Biomarker-specific reagent + 2° specific detection reagent + 3° specific detection reagent-Enzyme conjugate + QM-Enzyme conjugate + Fluorophore<br>Biomarker-specific reagent + 2° specific detection reagent + 3° specific detection reagent-Enzyme conjugate + Tyramide-Enzyme conjugate + DAB<br>Biomarker-specific reagent + 2° specific detection reagent + 3° specific detection reagent-Enzyme conjugate + Tyramide-Enzyme conjugate + Chromogen<br>Biomarker-specific reagent + 2° specific detection reagent + 3° specific detection reagent-Enzyme conjugate + Tyramide-Enzyme conjugate + Fluorophore |

TABLE 4-continued

| | |
|---|---|
| K3. Signaling conjugate comprises enzyme that reacts with second signaling conjugate comprising detectable moiety | Biomarker-specific reagent + 2° specific detection reagent + 3° specific detection reagent-Enzyme conjugate + QM-Enzyme conjugate + QM-Dye conjugate<br>Biomarker-specific reagent + 2° specific detection reagent + 3° specific detection reagent-Enzyme conjugate + QM-Enzyme conjugate + Tyramide-Dye conjugate<br>Biomarker-specific reagent + 2° specific detection reagent + 3° specific detection reagent-Enzyme conjugate + Tyramide-Enzyme conjugate + QM-Dye conjugate<br>Biomarker-specific reagent + 2° specific detection reagent + 3° specific detection reagent-Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent-Enzyme conjugate + Tyramide-(biotin or hapten) conjugate + Dye-(avidin or anti-hapten specific detection reagent) conjugate<br>Biomarker-specific reagent + 2° specific detection reagent + 3° specific detection reagent-Enzyme conjugate + QM-(biotin or hapten) conjugate + Dye-(avidin or anti-hapten specific detection reagent) conjugate |
| K5. Signaling conjugate comprises member of a specific binding pair and other member of binding pair is linked to enzyme reactive with detectable moiety | Biomarker-specific reagent + 2° specific detection reagent + 3° specific detection reagent-Enzyme conjugate + QM-(biotin or hapten) conjugate + Enzyme-(avidin or anti-hapten specific detection reagent) conjugate + DAB<br>Biomarker-specific reagent + 2° specific detection reagent + 3° specific detection reagent-Enzyme conjugate + QM-(biotin or hapten) conjugate + Enzyme-(avidin or anti-hapten specific detection reagent) conjugate + Chromogen<br>Biomarker-specific reagent + 2° specific detection reagent + 3° specific detection reagent-Enzyme conjugate + QM-(biotin or hapten) conjugate + Enzyme-(avidin or anti-hapten specific detection reagent) conjugate + Fluorophore<br>Biomarker-specific reagent + 2° specific detection reagent + 3° specific detection reagent-Enzyme conjugate + Tyramide-(biotin or hapten) conjugate + Enzyme-(avidin or anti-hapten specific detection reagent) conjugate + DAB<br>Biomarker-specific reagent + 2° specific detection reagent + 3° specific detection reagent-Enzyme conjugate + Tyramide-(biotin or hapten) conjugate + Enzyme-(avidin or anti-hapten specific detection reagent) conjugate + Chromogen<br>Biomarker-specific reagent + 2° specific detection reagent + 3° specific detection reagent-Enzyme conjugate + Tyramide-(biotin or hapten) conjugate + Enzyme-(avidin or anti-hapten specific detection reagent) conjugate + Fluorophore |
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent-Enzyme conjugate + QM-(biotin or hapten) conjugate + Enzyme-(avidin or anti-hapten specific detection reagent) conjugate + Tyramide-Dye conjugate<br>Biomarker-specific reagent + 2° specific detection reagent + 3° specific detection reagent-Enzyme conjugate + QM-(biotin or hapten) conjugate + Enzyme-(avidin or anti-hapten specific detection reagent) conjugate + QM-Dye conjugate<br>Biomarker-specific reagent + 2° specific detection reagent + 3° specific detection reagent-Enzyme conjugate + Tyramide-(biotin or hapten) conjugate + Enzyme-(avidin or anti-hapten specific detection reagent) conjugate + Tyramide-Dye conjugate<br>Biomarker-specific reagent + 2° specific detection reagent + 3° specific detection reagent-Enzyme conjugate + Tyramide-(biotin or hapten) conjugate + Enzyme-(avidin or anti-hapten specific detection reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin or hapten) conjugate + Dye-(avidin or anti-hapten specific detection reagent) conjugate |
| L2. Enzyme linked to other member of specific binding pair, wherein the enzyme is reactive with detectable moiety | Biomarker-specific reagent + 2° specific detection reagent + 3° specific detection reagent-(biotin or hapten) conjugate + Enzyme-(avidin or anti-hapten specific detection reagent) conjugate + DAB<br>Biomarker-specific reagent + 2° specific detection reagent + 3° specific detection reagent-(biotin or hapten) conjugate + Enzyme-(avidin or anti-hapten specific detection reagent) conjugate + Chromogen<br>Biomarker-specific reagent + 2° specific detection reagent + 3° specific detection reagent-(biotin or hapten) conjugate + Enzyme-(avidin or anti-hapten specific detection reagent) conjugate + Fluorophore<br>Biomarker-specific reagent + 2° specific detection reagent + 3° specific detection reagent-(biotin or hapten) conjugate + Enzyme-(avidin or anti-hapten specific detection reagent) conjugate + QM-Dye conjugate |

TABLE 4-continued

| Biomarker-specific reagent + 2° specific detection reagent + 3° specific detection reagent-(biotin or hapten) conjugate + Enzyme-(avidin or anti-hapten specific detection reagent) conjugate + Tyramide-Dye conjugate |
| --- |

In a specific embodiment, the biomarker-specific reagents and the specific detection reagents set forth in Table 4 are antibodies. As would be appreciated by a person having ordinary skill in the art, the detection scheme for each of the biomarker-specific reagent may be the same, or it may be different.

Non-limiting examples of commercially available detection reagents or kits comprising detection reagents suitable for use with present methods include: VENTANA ultra View detection systems (secondary antibodies conjugated to enzymes, including HRP and AP); VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Arizona); PowerVision and PowerVision+IHC Detection Systems (secondary antibodies directly polymerized with HRP or AP into compact polymers bearing a high ratio of enzymes to antibodies); and DAKO EnVision™+System (enzyme labeled polymer that is conjugated to secondary antibodies).

If desired, the biomarker-stained slides may be counterstained to assist in identifying morphologically relevant areas. Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4',6-diamino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III. Staining Evaluation

In an embodiment, a set of stained samples generated by the presently disclosed methods are used to determine the presence or absence of a fusion protein in a patient sample. In the typical case, a sample obtained from a patient and prepared for analysis as set forth above. One portion of the sample (for example, a first tissue section of a biopsy of tumor resection sample, or a first slide prepared from a cytological sample of tumor cells (such as cellular smears (such as cervical smears), fine needle aspirates, isolated circulating tumor cells and the like) are prepared and stained with the biomarker-specific reagent. The stained samples are then scored for the percentage of cells staining and/or the percentage of cells staining at or above a pre-determined threshold level. Preferably, the samples are fixed in a formalin solution. In an embodiment, the threshold staining intensity is at least 1.5+ and the threshold level of tumor cells having the threshold staining intensity is in the range of 25% to 75%. In an embodiment, the threshold staining intensity is at least 1.5+ and the threshold level of tumor cells having the threshold staining intensity is 50%. In an embodiment, the threshold staining intensity is at least 1.5+ and the threshold level of tumor cells having the threshold staining intensity is 60%. In an embodiment, the threshold staining intensity is at least 1.5+ and the threshold level of tumor cells having the threshold staining intensity is 75%. In an embodiment, the threshold staining intensity is at least 2+ and the threshold level of tumor cells having the threshold staining intensity is in the range of 25% to 75%. In an embodiment, the threshold staining intensity is at least 2+ and the threshold level of tumor cells having the threshold staining intensity is 50%. In an embodiment, the threshold staining intensity is at least 2+ and the threshold level of tumor cells having the threshold staining intensity is 60%. In an embodiment, the threshold staining intensity is at least 2+ and the threshold level of tumor cells having the threshold staining intensity is 75%.

In some cases, the stained samples are stratified on the basis of expression pattern and then scored with a scoring methodology specific to the staining pattern. For example, where fixation gradients are observed, a first scoring methodology is applied to samples having a cytoplasmic and/or membranous expression pattern, and a second scoring methodology is applied to samples having a nuclear cellular localization. For example, samples having a cytoplasmic and/or membranous staining pattern may be scored by determining whether the sample meets or exceeds a threshold level of tumor cells at or above a threshold staining intensity, which are considered to be TRK fusion protein positive. In an embodiment, the threshold staining intensity is at least 1.5+ and the threshold level of tumor cells having the threshold staining intensity is in the range of 25% to 75%. In an embodiment, the threshold staining intensity is at least 1.5+ and the threshold level of tumor cells having the threshold staining intensity is 50%. In an embodiment, the threshold staining intensity is at least 1.5+ and the threshold level of tumor cells having the threshold staining intensity is 60%. In an embodiment, the threshold staining intensity is at least 1.5+ and the threshold level of tumor cells having the threshold staining intensity is 75%. In an embodiment, the threshold staining intensity is at least 2+ and the threshold level of tumor cells having the threshold staining intensity is in the range of 25% to 75%. In an embodiment, the threshold staining intensity is at least 2+ and the threshold level of tumor cells having the threshold staining intensity is 50%. In an embodiment, the threshold staining intensity is at least 2+ and the threshold level of tumor cells having the threshold staining intensity is 60%. In an embodiment, the threshold staining intensity is at least 2+ and the threshold level of tumor cells having the threshold staining intensity is 75%.

As another example, samples having a nuclear staining pattern may be scored by determining whether a minimum contiguous tumor cell area of the sample has a concentration of tumor cells staining at or above a threshold expression level. In an embodiment, the threshold contiguous tumor cell area is at least 20 cells, the threshold stain intensity is any specific staining over background, and the threshold percentage of cells is in the range of 25% to 75% or 25% to 80%. In another embodiment, the threshold contiguous tumor cell area is at least 20 cells, the threshold stain intensity is any specific staining over background, and the threshold percentage of cells is at least 75%. In another embodiment, the threshold contiguous tumor cell area is at least 20 cells, the threshold stain intensity is any specific staining over background, and the threshold percentage of cells is at least 80%. In an embodiment, the threshold contiguous tumor cell area is at least 20 cells, the threshold stain intensity is ≥0.5+, and the threshold percentage of cells is in the range of 25% to 75% or 25% to 80%. In another embodiment, the threshold contiguous tumor cell area is at least 20 cells, the threshold stain intensity is ≥0.5+, and the threshold percentage of cells is at least 75%. In another embodiment, the threshold contiguous tumor cell area is at least 20 cells, the threshold stain intensity is ≥0.5+, and the threshold percentage of cells is at least 80%. In an embodiment, the threshold contiguous tumor cell area is at least 50 cells, the threshold stain intensity is any specific staining over background, and the threshold percentage of cells is in the range of 25% to 75% or 25% to 80%. In another embodiment, the threshold contiguous tumor cell area is at least 50 cells, the threshold stain intensity is any specific staining over background, and the threshold percentage of cells is at least 75%. In another embodiment, the threshold contiguous tumor cell area is at least 50 cells, the threshold stain intensity is any specific staining over background, and the threshold percentage of cells is at least 80%. In an embodiment, the threshold contiguous tumor cell area is at least 50 cells, the threshold stain intensity is ≥0.5+, and the threshold percentage of cells is in the range of 25% to 75% or 25% to 80%. In another embodiment, the threshold contiguous tumor cell area is at least 50 cells, the threshold stain intensity is ≥0.5+, and the threshold percentage of cells is at least 75%. In another embodiment, the threshold contiguous tumor cell area is at least 50 cells, the threshold stain intensity is ≥0.5+, and the threshold percentage of cells is at least 80%.

VI. Clinical Application

In an embodiment, the assay as described herein is used to characterize a tumor sample from a patient. For example, a biopsy section or a resection sample is obtained, fixed, embedded in paraffin, sectioned, and stained. Stained sections are scored as described above. In some embodiments, a tumor having a score indicative of the presence of a fusion protein is characterized as "fusion positive," while a tumor having a score that is not indicative of the presence of a fusion protein is characterized as "fusion negative." In other embodiments, an intermediate category of cells between "fusion positive" and "fusion negative" is characterized as "equivocal." For example, where the scoring methodology is based on a threshold percentage of cells staining at or above a threshold level, a range of percentages below the threshold percentage may be defined as "equivocal," and all other samples having a percentage of cells falling below the equivocal range are deemed "fusion negative." As another example, where the scoring methodology is based on a threshold percentage of cells staining at or above a threshold level within a threshold tumor cell area, a range of percentages below the threshold tumor cell area may be defined as "equivocal," and all other samples having a percentage of cells falling below the equivocal range are deemed "fusion negative."

In some embodiments, the assay is used as a screening test to identify patients eligible for a nucleic acid-based assay to confirm the presence of the fusion protein. For example, samples may be screened for the presence or absence of a fusion protein using the assay, and only those samples that are characterized as fusion positive are subjected to a sequencing-based or PCR-based assay to confirm the presence and/or identity of the fusion that is was detected in the assay. In other embodiments, the assay is a reflex test to confirm the presence and expression of a fusion protein identified by a nucleic acid-based assay. For example, samples may be screened for the presence or absence of a NTRK gene rearrangement using a sequencing-based or PCR-based assay, and only those samples that are characterized as rearrangement-positive by the sequencing-based or PCR-based assay are screened by the assay described herein to confirm the presence and/or expression of the fusion detected by the nucleic acid assay. In other embodiments, characterization of the presence or absence of a fusion protein is made solely on the basis of the assay. In yet other embodiments, samples characterized as "fusion negative" or "equivocal" may be screened for the presence of an NTRK gene rearrangement by a sequencing-based or PCR-based assay, and cells that are characterized as "fusion positive" are not.

In some embodiments, the assay is used to select a therapy for the patient. For example, a patient having a tumor or sample characterized as "fusion positive" receives a targeted therapy directed against the wild-type counterpart, optionally in combination with a standard treatment course for the tumor. Exemplary targeted therapies include those recited in Table 5:

TABLE 5

| Drug type | Exemplary active ingredients or compound class |
|---|---|
| Small molecule tyrosine kinase inhibitor | aliratinib; belizatinib; cabozantinib; dovitinib; DS-6052B; entrectinib; F17752; LOXO-101 (larotrectinib); milciclib; PLX7486; sitrivatinib |

A patient having a tumor or sample characterized as fusion negative receives a standard therapy, without inclusion of a targeted therapy for the wild-type counterpart.

VIII. Examples

To assess whether a scoring algorithm could be developed that could predict the presence of Trk fusions across tumor types, IHC staining and analysis of greater than 3000 tissues across multiple indications was conducted.

Formalin-fixed, paraffin-embedded (FFPE) normal and neoplastic tissues were commercially acquired. Tissues were screened with a prototype IHC assay with a pan-TRK antibody clone EPR17341, comprising heat induced epitope retrieval followed by antibody incubation and colormetric development using OptiView DAB Detection (RTD, Tucson, Arizona) on a BenchMark ULTRA automated slide stainer (RTD, Tucson Arizona).

A subset of cases, the majority having specific staining by the pan-TRK (EPR17341) assay, were further evaluated with in situ hybridization (ISH) with break-apart probes for NTRK1, 2 and 3. The NTRK1, 2, and 3 Break-Apart Oligo Probes each consist of two pools of oligonucleotides (oligos) targeting the genomic regions across the 5' and 3' ends of the NTRK1, 2, and 3 genes. DNP and Fluorescein haptens were attached to oligos in a basic insertion configuration during synthesis using DNP-TEG phosphoramidite (Link Technologies Ltd, Bellshill, Lanarkshire) and 6-fluorescein phosphoramidite (Link Technologies Ltd, Bellshill, Lanarkshire).

Figure 2B:
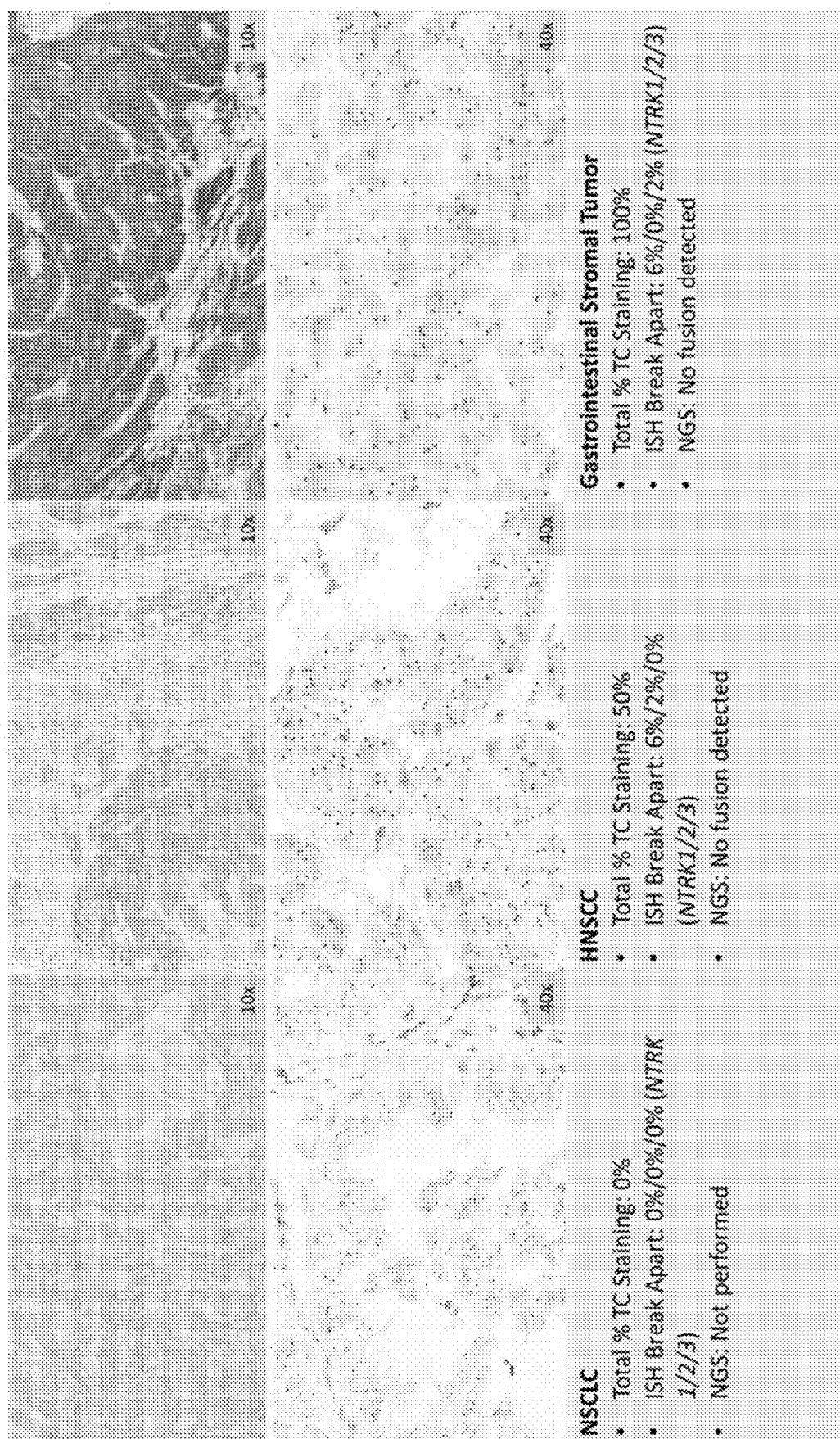
FIG. 2B IHC results for Trk-fusions in multiple tumor types. Orthogonal testing methods were used to assess for absence of Trk fusions.

Representative images of pan-TRK staining across different tumor types with various genotypes are shown in FIGS. 2A-2B. 9% (n=324) of tumors demonstrated specific pan-TRK IHC staining when defined as >0% of tumor cell staining (range: 0%-54% in gastric cancers and salivary gland cancers, respectively). The overall percentage of cases with specific staining decreased to 5% (n=191) and 4% (n=133) when only considering specimens with IHC specific staining in ≥10% and ≥25% of tumor cells, respectively.

164 cases demonstrating any staining by IHC were available for ISH testing. Of these, 12 were found to harbor NTRK fusions (5 CRC, 2 melanoma, 2 papillary thyroid cancers, 2 salivary gland cancers and 1 pancreatic cancer). The rate of pan-TRK positive cases at various tumor cell staining percentages by tumor type including results of confirmatory testing by ISH is shown at Table 6:

TABLE 6

| Tumor | No stain | >0% | >1% | >5% | >10% | >25% | >50% | >75% | A | B | C | D |
|---|---|---|---|---|---|---|---|---|---|---|---|---|
| PC (162) | 95% | 5% | 5% | 5% | 5% | 3% | 1% | 1% | 8 | 1 | 1 | 100% |
| CRC (208) | 94% | 6% | 6% | 4% | 3% | 2% | 2% | 2% | 13 | 7 | 5 | 71% |
| MN (444) | 96% | 4% | 4% | 2% | 2% | 1% | 1% | 0% | 19 | 6 | 2 | 33% |
| PTT (111) | 89% | 11% | 11% | 11% | 11% | 10% | 8% | 7% | 12 | 6 | 2 | 33% |
| SGT (61) | 46% | 54% | 54% | 44% | 44% | 33% | 18% | 3% | 33 | 8 | 0 | 25% |
| CAC (155) | 98% | 2% | 0% | 0% | 0% | 0% | 0% | 0% | 3 | 3 | 0 | 0% |
| HCC (95) | 97% | 3% | 3% | 2% | 2% | 1% | 0% | 0% | 3 | 3 | 0 | 0% |
| UC (131) | 96% | 4% | 3% | 3% | 3% | 2% | 0% | 0% | 5 | 5 | 0 | 0% |
| NSCLC (1366) | 93% | 7% | 6% | 4% | 3% | 2% | 1% | 0% | 97 | 64 | 0 | 0% |
| Breast (421) | 90% | 10% | 8% | 6% | 5% | 3% | 2% | 1% | 42 | 15 | 0 | 0% |
| HNSCC (125) | 82% | 18% | 17% | 10% | 10% | 6% | 4% | 0% | 22 | 11 | 0 | 0% |
| GB (18) | 78% | 22% | 22% | 17% | 17% | 11% | 11% | 0% | 4 | 1 | 0 | 0% |
| SCN (130) | 77% | 23% | 21% | 18% | 17% | 16% | 13% | 9% | 32 | 18 | 0 | 0% |
| NET (53) | 47% | 53% | 51% | 49% | 43% | 36% | 30% | 13% | 29 | 16 | 0 | 0% |
| GC (31) | 100% | 0% | 0% | 0% | 0% | 0% | 0% | 0% | 0 | 0 | 0 | |
| PC (12) | 100% | 0% | 0% | 0% | 0% | 0% | 0% | 0% | 0 | 0 | 0 | |
| RCC (20) | 95% | 5% | 5% | 5% | 5% | 5% | 5% | 0% | 1 | 0 | 0 | |
| EOC (12) | 92% | 8% | 8% | 0% | 0% | 0% | 0% | 0% | 1 | 0 | 0 | |

PC = Pancreatic cancer;
CRC = colorectal cancer;
PTT = Papillary Thyroid Tumor;
MN = Melanoma;
SGT = Salivary Gland Tumor;
CAC = Cholangiocarcinoma;
HCC = Hepatocellular carcinoma;
UC = Urothelial Carcinoma;
NSCLC = Non-small cell lung carcinoma;
HNSCC = Head and neck squamous cell carcinoma;
GB = Glioblastoma;
SCN = Spindle Cell Neoplasm (including GIST);
NET = Neuroendocrine Tumors;
GC = Gastric Carcinoma;
PC = Prostatic Carcinoma;
RCC = Renal cell carcinoma;
EOC = Epithelial Ovarian Carcinoma;
A = # IHC positive;
B = # tested by ISH;
C = # fusion positive by ISH;
D = % IHC+ confirmed as fusion+

Synthesized oligos were purified using reverse-phase cartridges and mass spectrometry was performed to verify removal of truncated oligos.

Criteria used to define break-apart status for the ISH assays were determined based on evaluation of average break-apart rates in normal tissues and in tumors without pan-TRK IHC expression. Tumors in which break-apart rates were greater than 5 standard deviations above the average were considered to represent true NTRK gene fusions.

Figure 3A:
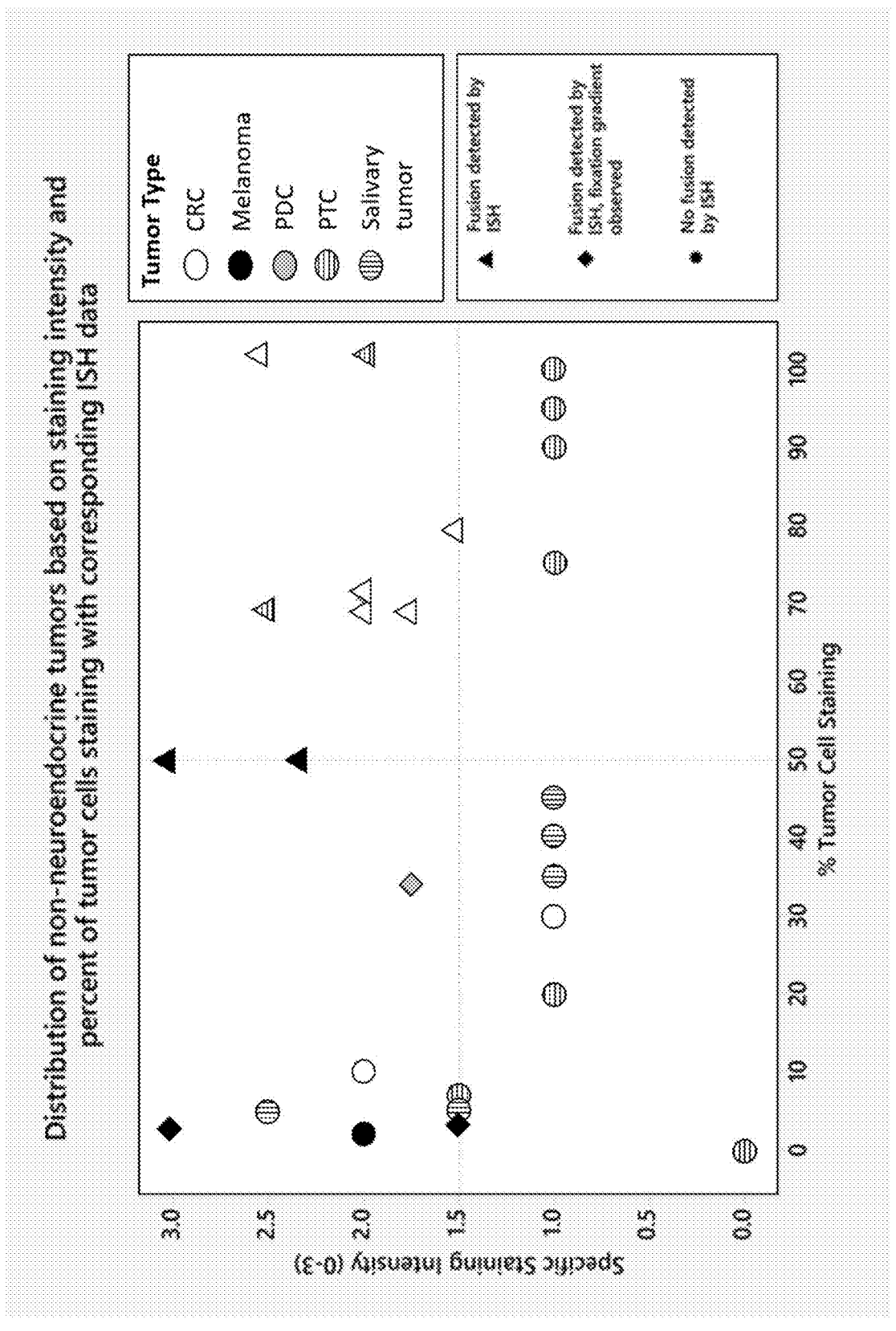
FIG. 3A The staining distribution of tumor types with ISH-confirmed fusion-positive cases in the dataset by percentage of tumor cells staining (0-100%) and by intensity of the staining (0-3+). Circles depict fusion-negative cases while triangles represent fusion-positive cases. Diamonds indicate cases in which fusions were detected by ISH, but fixation gradient was observed. Patterns represent various tumor histologies.
Figure 3B:
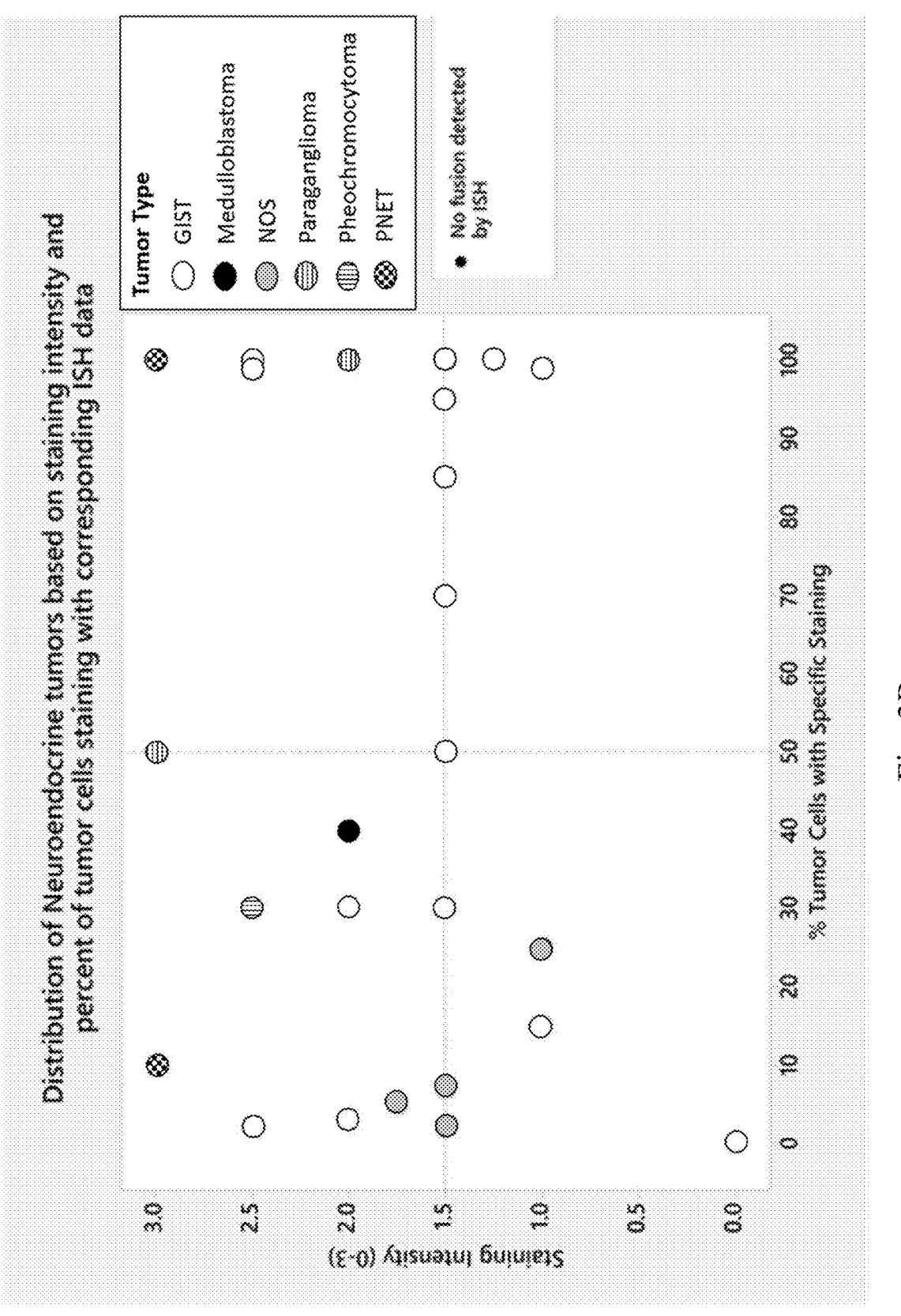
FIG. 3B The staining distribution of tumor types with ISH-confirmed fusion-negative cases in the dataset by percentage of tumor cells staining (0-100%) and by intensity of the staining (0-3+).

Intensity of staining and percent tumor cells staining varied by tissue type but cases found to harbor fusions tended to have higher intensity staining and a greater percentage of tumor cells staining (see FIGS. 3A & 3B). FIGS. 3A and 3B show the distribution of ISH-confirmed samples by percentage of tumor cells staining (0-100%) and by intensity of the staining (0-3+). Circles depict fusion-negative cases while triangles represent fusion-positive cases. Colors represent various tumor histologies. FIG. 3A shows the staining distribution of tumor types with ISH-confirmed fusion-positive cases in the dataset and FIG. 3B shows the staining distribution of neuroendocrine tumors where no fusion-positive cases were detected.

Results by percent of tumor cells staining by IHC in all tumors in the dataset are shown at Table 7:

TABLE 7

| % tumor cells staining by IHC | Positive IHC | Available for ISH confirmation | Positive by ISH | % positive by IHC and ISH | Positive cases not detected at this IHC percentage |
|---|---|---|---|---|---|
| >0% | 324 | 164 | 12 | 7.3% | NA |
| >1% | 288 | 139 | 12 | 8.6% | NA |
| >5% | 222 | 133 | 12 | 9.0% | NA |
| >10% | 191 | 122 | 10 | 8.2% | Melanoma |
| >25% | 133 | 88 | 10 | 11.4% | Melanoma |
| >50% | 91 | 56 | 9 | 16.1% | Melanoma, pancreas |
| >75% | 45 | 34 | 7 | 20.6% | Melanoma (2), pancreas, PTC and salivary gland |

12/164 (7%) of cases, for which the IHC specific staining was >0% of tumor cells, demonstrated the presence of an NTRK fusion by ISH. 10/88 (11%) of cases, for which IHC specific staining was >25% of tumor cells, demonstrated presence of fusion by ISH (Table 6). Tumors showing fusions by ISH tended to stain at higher intensity and higher tumor percentage by pan-TRK IHC (upper right-hand quadrant; FIG. 3A) than did non-fusion tumors, the exception being neuroendocrine tumors (FIG. 3B). Using the higher definition of IHC specific positive staining (>25%) would have resulted in two fusion-positive melanomas being excluded from ISH testing (Table 6). These two tissue samples stained poorly by IHC, demonstrating evidence of fixation gradients. Importantly, these tissues did exhibit nuclear staining of high intensity in areas that were not affected by fixation-related artifact, in a high percentage (>90%) of contiguous cells.

Figure 4:
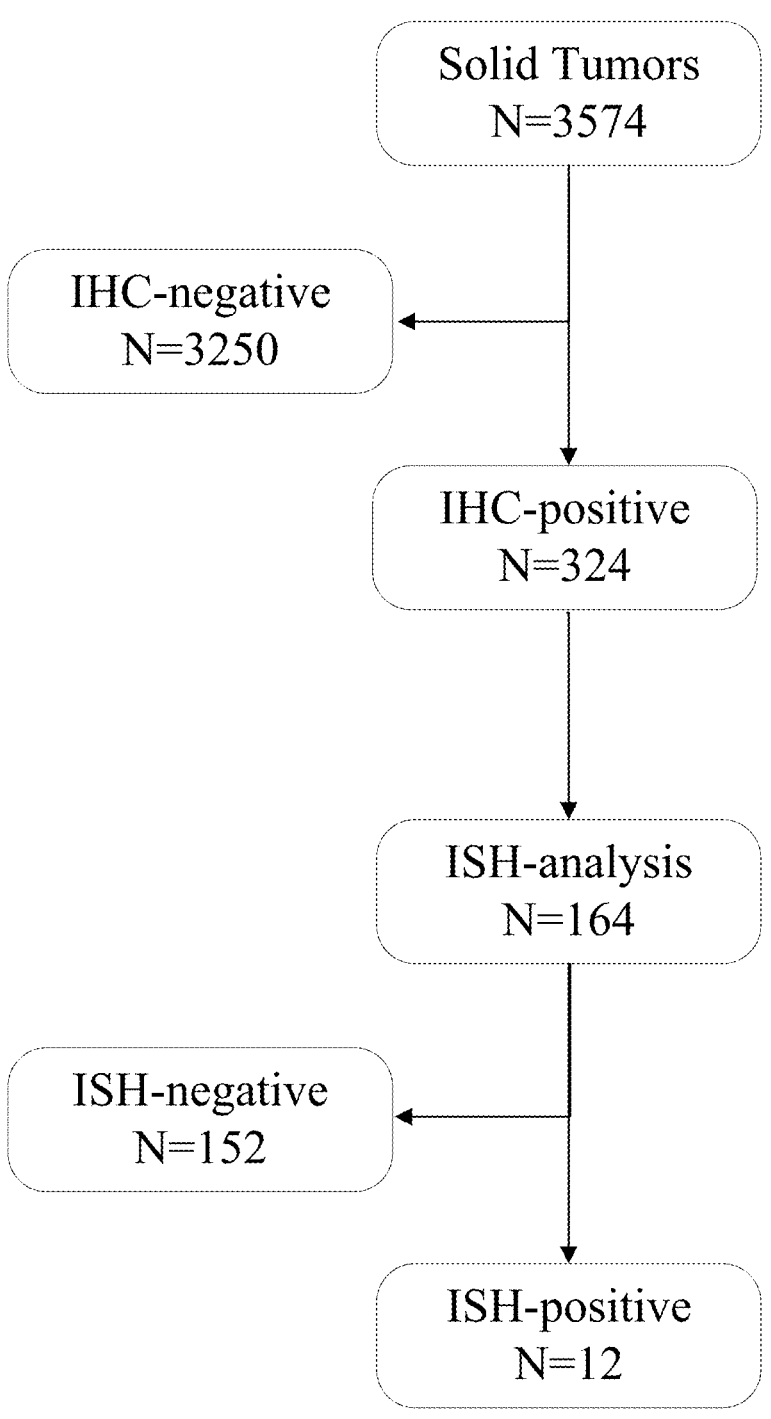
FIG. 4 Sub-categorization of solid tumors based on IHC and ISH testing.

A sub-categorization of solid tumors based on IHC and ISH testing is illustrated at FIG. 4.

Figure 5:
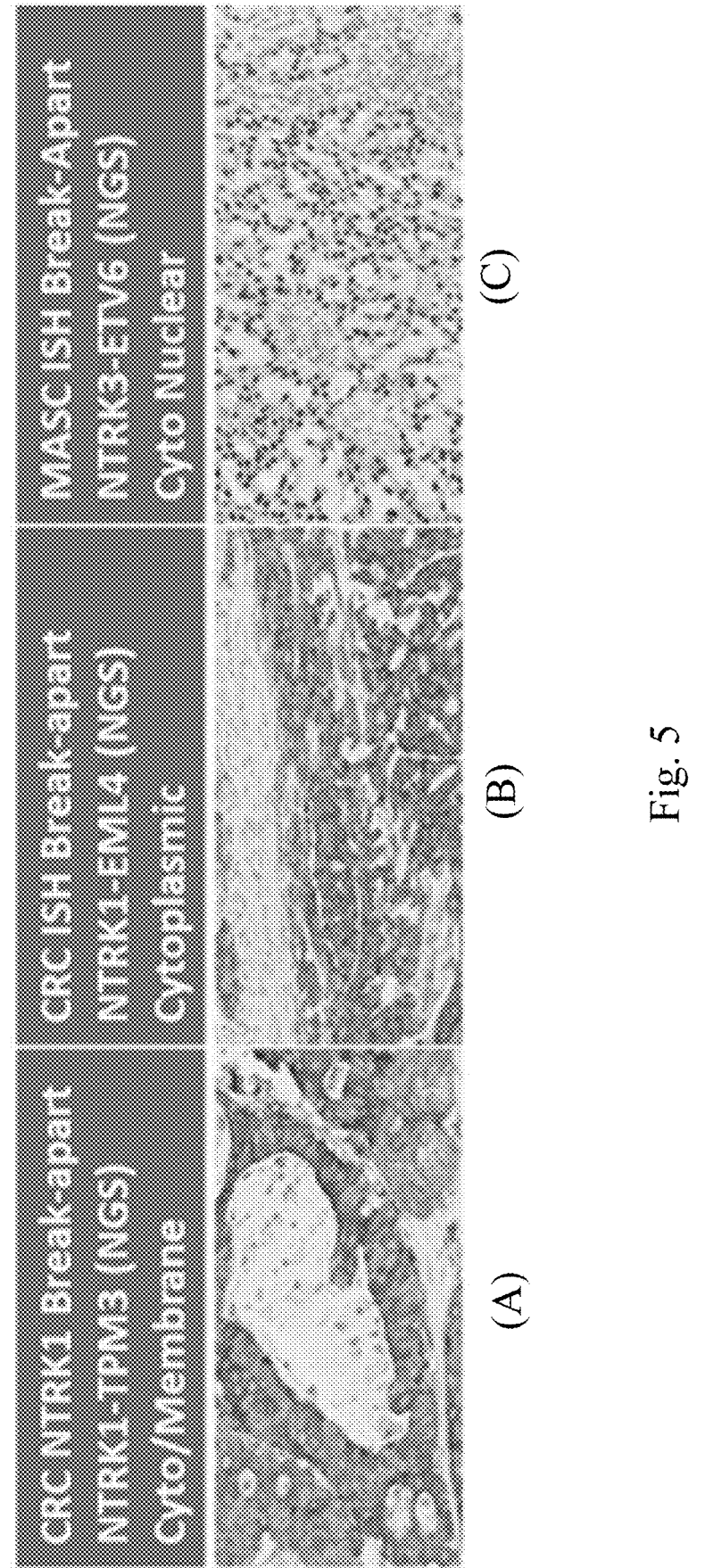
FIG. 5 Examples of differences in staining pattern localizations obtained with the staining methods described herein. (A) Cytoplasmic/membranous staining pattern in a colorectal tumor determined to have a NTRKI rearrangement by break-apart in situ hybridization assay, confirmed to be a NTRK1-TPM3 fusion by next-generation sequencing. (B) Cytoplasmic staining pattern in a colorectal tumor determined to have a NTRKI rearrangement by break-apart in situ hybridization assay, confirmed to be a NTRK1-EML4 fusion by next-generation sequencing. (C) Nuclear/cytoplasmic staining pattern in a mammary analogue secretory carcinoma (MASC) determined to have a NTRK3 rearrangement by break-apart in situ hybridization assay, confirmed to be a NTRK3-ETV6 fusion by next-generation sequencing.
Figure 6:
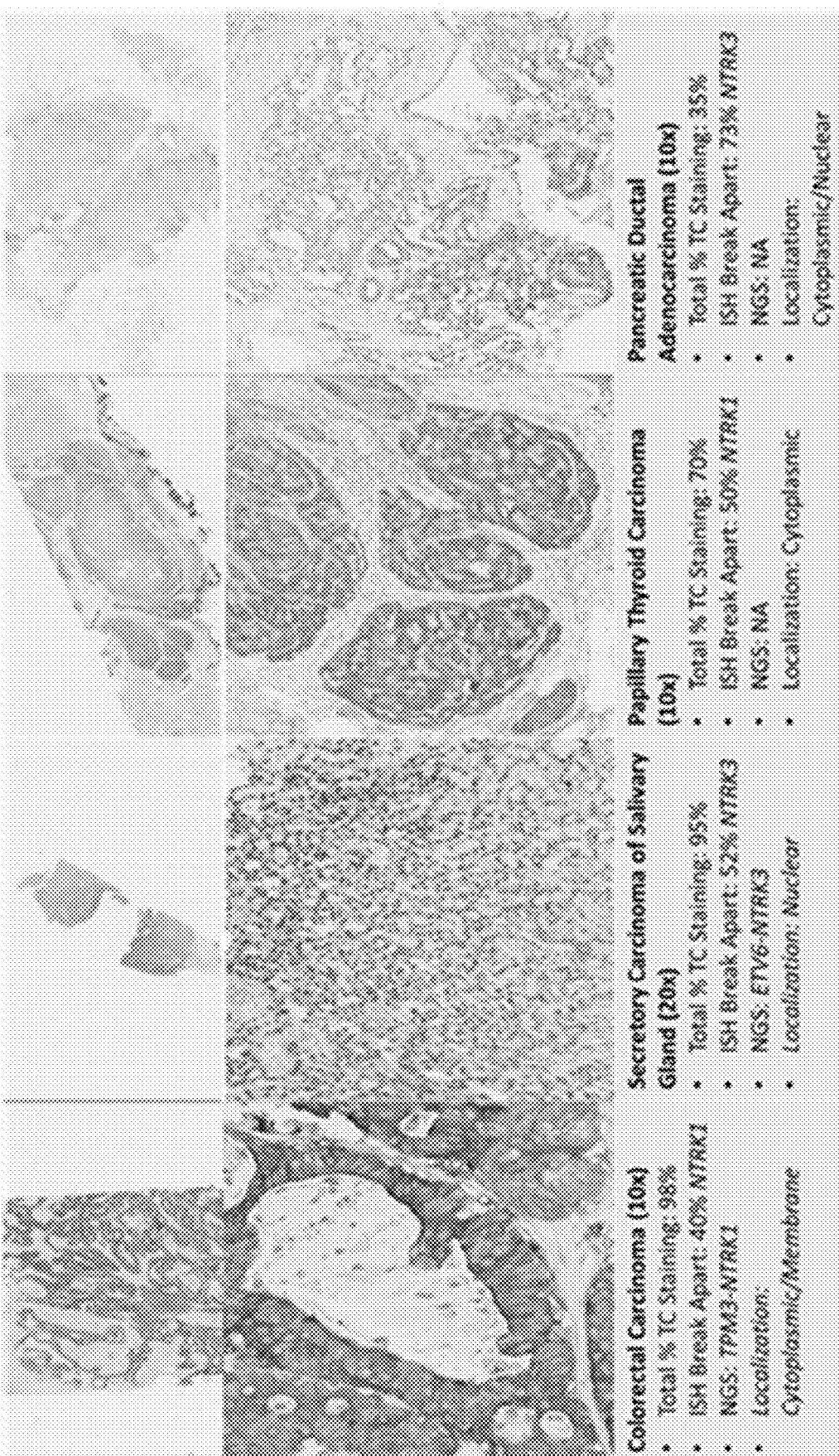
FIG. 6 Examples of fixation gradients in the tissues and demonstration that nuclear localizations appear to be more affected by the gradients than the cytoplasmic/membrane localizations. Bottom row shows low magnification and top row shows high magnification of a subsection of the image immediately below.

Examples of staining patterns observed are illustrated at FIG. 5 and FIG. 6. As shown at FIG. 5, staining patterns could include aspect of membranous staining (A), cytoplasmic staining (A-C) and nuclear staining (C). FIG. 7 shows that some samples experienced fixation gradients, which could affect staining levels of some cells. It was noted that samples with nuclear localization were more sensitive to fixation gradients than samples having a cytoplasmic/membrane localization.

In sum, pan-TRK IHC staining varies in both intensity and in percentage of tumor cells staining across tumor types. Solid tumors harboring fusions based on ISH showed IHC staining with higher intensity and in a greater percentage of tumor cells than did tumors with wild-type TRK protein expression, with the exception of neuroendocrine and spindle cell tumors. In tumor types with low prevalence of wild-type TRK protein expression (e.g. CRC and papillary thyroid cancer) pan-TRK IHC staining may be useful in helping to identifying tumors harboring fusions. By contrast, in tumors with high prevalence of wild-type TRK protein expression (e.g. neuroendocrine tumors, GIST) the distribution of IHC staining percentage and intensity did not support clear differentiation between wild-type expression and fusion. Per Table 6, as the percentage of tumor cell staining with pan-TRK IHC increased, the number of specimens (out of the total 164 cases) that were subjected to ISH progressively decreased; this decrease, however, did not compromise identification of tumors with NTRK gene fusion by ISH in well-preserved tissues. This metric, combined with increased IHC staining intensity seem to further highlight those tumors with NTRK gene fusion by ISH testing.

Two melanomas and one pancreatic ductal adenocarcinoma did not follow the above observations. The observed lower percentages of tumor cell staining were likely related to fixation artifacts. Interestingly however, small areas of contiguous viable tumor did demonstrate high percentages of nuclear staining at high intensity.

VI. Additional Disclosed Embodiments

The following exemplary embodiments shall be included as part of this disclosure:

Embodiment 1. A method of detecting a fusion protein of TrkA, TrkB, or TrkC in a non-neuroendocrine tumor sample, the method comprising:

affinity histochemically staining the sample with a biomarker-specific reagent that specifically binds to one or more of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3;

detecting a staining pattern in the sample; and scoring the sample as positive for a fusion protein involving TrkA, TrkB, or TrkC if the sample has a staining pattern in which greater than or equal to a threshold percentage of tumor cells stain above a threshold specific staining intensity.

Embodiment 2. The method of Embodiment 1, wherein the percentage of tumor cells staining above the threshold specific staining intensity is a percentage of tumor cells in the entire tumor area.

Embodiment 3. The method of any one of Embodiments 1 and 2, wherein the threshold percentage of tumor cells is in the range of 50% to 75% and the threshold staining intensity is at least 1.5.

Embodiment 4. The method of Embodiment 3, wherein the threshold percentage of tumor cells is 50% and the threshold staining intensity is 1.75.

Embodiment 5. The method of Embodiment 3, wherein the threshold percentage of tumor cells is 60% and the threshold staining intensity is 1.75.

Embodiment 6. The method of Embodiment 3, wherein the threshold percentage of tumor cells is 75% and the threshold staining intensity is 1.75.

Embodiment 7. The method of Embodiment 3, wherein the threshold percentage of tumor cells is 50% and the threshold staining intensity is 2.

Embodiment 8. The method of Embodiment 3, wherein the threshold percentage of tumor cells is 60% and the threshold staining intensity is 2.

Embodiment 9. The method of Embodiment 3, wherein the threshold percentage of tumor cells is 75% and the threshold staining intensity is 2.

Embodiment 10. The method of Embodiment 3, wherein the threshold percentage of tumor cells is 50% and the threshold staining intensity is 3.

Embodiment 11. The method of Embodiment 3, wherein the threshold percentage of tumor cells is 60% and the threshold staining intensity is 3.

Embodiment 12. The method of Embodiment 3, wherein the threshold percentage of tumor cells is 75% and the threshold staining intensity is 3.

Embodiment 13. The method of any one of Embodiments 2 to 12, wherein the sample has a membranous and/or cytoplasmic staining pattern.

Embodiment 14. The method of any one of Embodiments 1 to 13, wherein the percentage of tumor cells staining above the threshold specific staining intensity is a percentage of tumor cells within a tumor cell area having a threshold level of contiguous tumor cells.

Embodiment 15. The method of Embodiment 14, wherein the threshold level of contiguous tumor cells is at least 20 contiguous cells, the threshold percentage of cells is in the range of 20% to 90%, and the threshold staining intensity is any specific staining above background.

Embodiment 16. The method of Embodiment 14, wherein the threshold level of contiguous tumor cells is at least 20 contiguous cells, the threshold percentage of cells is in the range of 20% to 90%, and the threshold staining intensity is 0.5.

Embodiment 17. The method of Embodiment 14, wherein the threshold level of contiguous tumor cells is at least 50 contiguous cells and the threshold percentage of cells is at least 80%, and the threshold staining intensity is any specific staining above background.

Embodiment 18. The method of Embodiment 14, wherein the threshold level of contiguous tumor cells is at least 50 contiguous cells and the threshold percentage of cells is at least 80%, and the threshold staining intensity is 0.5.

Embodiment 19. The method of any one of Embodiments 14 to 18, wherein the sample has a nuclear staining pattern.

Embodiment 20. A method of detecting a fusion protein of TrkA, TrkB, or TrkC in a non-neuroendocrine tumor sample, the method comprising:

affinity histochemically staining the sample with a bio-marker-specific reagent that specifically binds to one or more of: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; or an amino acid sequence comprising, consisting essentially of, or consisting of residues 718-839 of SEQ ID NO: 3;

detecting staining pattern in the sample; and scoring the sample as positive for a fusion protein involving TrkA, TrkB, or TrkC if:

the sample has a cytoplasmic and/or membranous staining pattern and has a greater than or equal to a first threshold percentage of tumor cells staining above a first threshold staining intensity; or the sample has a nuclear staining pattern and greater than or equal to a second threshold percentage of cells within a threshold tumor cell area that are specifically stained at a second staining intensity.

Embodiment 21. The method of Embodiment 20, wherein the first threshold percentage of tumor cells is in the range of 50% to 75% and the first threshold staining intensity is at least 1.5.

Embodiment 22. The method of Embodiment 20, wherein the first threshold percentage of tumor cells is 50% and the first threshold staining intensity is 1.75.

Embodiment 23. The method of Embodiment 20, wherein the first threshold percentage of tumor cells is 60% and the first threshold staining intensity is 1.75.

Embodiment 24. The method of Embodiment 20, wherein the first threshold percentage of tumor cells is 75% and the first threshold staining intensity is 1.75.

Embodiment 25. The method of Embodiment 20, wherein the first threshold percentage of tumor cells is 50% and the first threshold staining intensity is 2.

Embodiment 26. The method of Embodiment 20, wherein the first threshold percentage of tumor cells is 60% and the first threshold staining intensity is 2.

Embodiment 27. The method of Embodiment 20, wherein the first threshold percentage of tumor cells is 75% and the first threshold staining intensity is 2.

Embodiment 28. The method of Embodiment 20, wherein the first threshold percentage of tumor cells is 50% and the first threshold staining intensity is 3.

Embodiment 29. The method of Embodiment 20, wherein the first threshold percentage of tumor cells is 60% and the first threshold staining intensity is 3.

Embodiment 30. The method of Embodiment 20, wherein the first threshold percentage of tumor cells is 75% and the first threshold staining intensity is 3.

Embodiment 31. The method of Embodiment 20, wherein the threshold tumor cell area is at least 20 contiguous cells, the second threshold percentage of cells is in the range of 20% to 90%, and the second threshold staining intensity is any specific staining above background.

Embodiment 32. The method of Embodiment 20, wherein the threshold tumor cell area is at least 20 contiguous cells, the second threshold percentage of cells is in the range of 20% to 90%, and the second threshold staining intensity is 0.5.

Embodiment 33. The method of Embodiment 20, wherein the threshold tumor cell area is at least 50 contiguous cells and the second threshold percentage of cells is at least 80%, and the second threshold staining intensity is any specific staining above background.

Embodiment 33. The method of Embodiment 20, wherein the threshold tumor cell area is at least 50 contiguous cells and the second threshold percentage of cells is at least 80%, and the second threshold staining intensity is 0.5.

Embodiment 34. The method of any one of Embodiments 1 to 33, wherein the biomarker-specific reagent specifically binds to: an amino acid sequence comprising, consisting essentially of, or consisting of residues 363-760 of SEQ ID NO: 1; an amino acid sequence comprising, consisting essentially of, or consisting of residues 646-838 of SEQ ID NO: 2; and an amino acid sequence comprising, consisting essentially of, or consisting of residues 718-839 of SEQ ID NO: 3.

Embodiment 35. The method of Embodiment 34, wherein the biomarker-specific reagent is an antibody.

Embodiment 36. The method of Embodiment 35, wherein the antibody is immunospecific for an epitope disposed in an amino acid sequence consisting of amino acids 816-838 of SEQ ID NO: 2.

Embodiment 37. The method of Embodiment 36, wherein the antibody is monoclonal antibody clone EPR17341.

Embodiment 38. The method of any one of Embodiments 34 to 37, wherein the affinity histochemically staining comprises:

(a) subjecting the sample to a heat-induced epitope retrieval process; and (b) contacting the sample with the biomarker-specific reagent and a set of detection reagents to deposit a brightfield dye in proximity to any biomarker-specific reagent bound to the sample.

Embodiment 39. The method of Embodiment 38, wherein (b) is a biomarker-specific reagent and detection reagent combination as set forth in Table 4.

US 12,631,634 B2

33

Embodiment 40. The method of Embodiment 38, wherein:

(b1) the biomarker specific reagent is an antibody that is specifically immunoreactive with each of: an amino acid sequence consisting of residue 363-760 of SEQ ID NO: 1; an amino acid sequence consisting of residues 646-838 of SEQ ID NO: 2; and an amino acid sequence consisting of residues 718-839 of SEQ ID NO: 3; and (b2) the set of detection reagents comprises a secondary antibody immunoreactive with the antibody of (b1), a tertiary antibody immunoreactive with the secondary antibody conjugated to an enzyme, and a set of reagents reactive with the enzyme to effect deposition of a brightfield dye on the sample.

Embodiment 41. The method of Embodiment 38, wherein the secondary antibody is haptenated and the tertiary antibody is an anti-hapten antibody.

Embodiment 42. The method of Embodiment 41, wherein the brightfield dye is 3,3'-diaminobenzidine (DAB).

Embodiment 43. A method of detecting an NTRK rearrangement in a non-neuroendocrine tumor sample, the method comprising detecting the presence of a Trk fusion protein in the sample according to the method of any one of Embodiments 1 to 42, and screening the sample for the NTRK rearrangement by sequencing, reverse transcriptase polymerase chain reaction, or in situ hybridization if the sample is scored as positive for a fusion protein involving TrkA, TrkB, or TrkC.

Embodiment 44. A method of detecting an NTRK rearrangement in a non-neuroendocrine tumor sample, the method comprising detecting the presence of a Trk fusion protein in the sample according to the method of any one of Embodiments 1 to 42, identifying samples as either Trk Fusion Positive or Trk Fusion Negative, and screening samples that are Trk Fusion Negative for the NTRK rearrangement by sequencing, reverse transcriptase polymerase chain reaction, or in situ hybridization.

Embodiment 45. A method of detecting an NTRK rearrangement in a non-neuroendocrine tumor sample, the method comprising detecting the presence of a Trk fusion protein in the sample according to the method of any one of Embodiments 1 to 42, identifying samples as either Trk Fusion Positive, Trk Fusion Equivocal, or Trk Fusion Negative, and screening samples that are Trk Fusion Equivocal for the NTRK rearrangement by sequencing, reverse transcriptase polymerase chain reaction, or in situ hybridization.

Embodiment 46. A method of selecting a patient to receive a Trk-directed therapy, comprising detecting the presence of a Trk fusion protein in a non-neuroendocrine tumor sample according to a method of any one of Embodiments 1 to 43, and selecting the patient to receive the therapy if the sample is scored as positive for a fusion protein involving TrkA, TrkB, or TrkC or the NTRK rearrangement is detected.

Embodiment 47. A method of selecting a patient to receive a Trk-directed therapy, comprising detecting the presence of a Trk fusion protein or an NTRK rearrangement in a non-neuroendocrine tumor sample according to the method of any one of Embodiments 44 to 45, and selecting the patient to receive the therapy if the sample is scored as positive for a fusion protein involving TrkA, TrkB, or TrkC or the NTRK rearrangement is detected.

The foregoing disclosure of the exemplary embodiments is for purposes of illustration and description. It is not intended to be an exhaustive list of embodiments of the invention or to limit the subject disclosure to the precise forms disclosed. Many variations and modifications of the embodiments described herein will be apparent to one of ordinary skill in the art in light of the above disclosure.

Further, in describing representative embodiments disclosed herein, the specification may have presented the method and/or process of the present subject disclosure as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present subject disclosure should not be limited to the performance of their steps in the order written unless explicitly stated or otherwise clear from the context, and one skilled in the art can readily appreciate that the sequences may be varied and still remain within the spirit and scope of the present subject disclosure.

VII. References

The following references are hereby incorporated by reference in their entirety:

Amatu et al., NTRK gene fusions as novel targets of cancer therapy across multiple tumour types, ESMO Open, Vol. 1, Issue 2, e000023 doi: 10.1136/esmoopen-2015-000023 (2016).

Bailey et al., Tropomyosin receptor kinase inhibitors: an updated patent review for 2010-2016-Part II, Expert Opinion on Therapeutic Patents, Vol. 27, Issue 7, pp. 831-49 (March 2017).

D'Amico et al., State of the art in antigen retrieval for immunohistochemistry, J Immunol Methods. Vol. 341 (1-2), pp. 1-18 (Feb. 28, 2009).

Hechtman et al., Pan-Trk Immunohistochemistry Is an Efficient and Reliable Screen for the Detection of NTRK Fusions, Am. J. Surg. Path., Vol. 41, Issue 11, pp. 1547-51 (November 2017).

Prichard, Overview of Automated Immunohistochemistry, Arch Pathol Lab Med., Vol. 138, pp. 1578-1582 (2014)

Shi et al., Antigen retrieval immunohistochemistry: review and future prospects in research and diagnosis over two decades, J Histochem Cytochem, Vol. 59, Issue 1, pp. 13-32 (January 2011).

Stransky et al., The landscape of kinase fusions in cancer, Nature Communications, Vol. 5, Article No. 4846 (2014) doi: 10.1038/ncomms5846.

Vinod et al., A simple and effective heat induced antigen retrieval method, MethodsX, Vol. 3, pp. 315-19 (published online Apr. 8, 2016).

Warford et al., Antigen retrieval, blocking, detection and visualisation systems in immunohistochemistry: A review and practical evaluation of tyramide and rolling circle amplification systems, Methods, Vol. 70, Issue 1, pp. 28-33 (November 2014).

Wellcome Sanger Institute, COSMIC—the Catalogue of Somatic Mutations in Cancer (COSMIC database), available at http://cancer.sanger.ac.uk/cosmic/fusion (last accessed 13 Sep. 2018).

Yamashita et al., Mechanisms of Heat-induced Antigen Retrieval: Analyses In Vitro Employing SDS-PAGE and Immunohistochemistry, J. Histochemistry and Cytochemistry, Vol. 53, Issue 1, pp. 13-21 (2005).

Barbacid M. et al. Biochim. Biophys. Acta Rev. Cancer 1991.

Barbacid M. Annals New York Academy of Sciences. 1995: 442-458.

Lemmon M A and Schlessinger J. Cell 2010; 141:1117-1134.

Klein R et al. Cell 1991; 85:189-197.

Eide F et al. J. Neurosci. 1996; 16 (10): 3123-3129.

Luberg K et al. BMC Neurosci. 2015:16:78 DOI 10.1186/s12868-015-0215-x.

Vaishnavi A, et al. Nature Medicine. 2013; 19 (11): 1469-1472.

De Braud F G et al. 2014 ASCO Annual Meeting; Abstract 2502.

Argani P M, et al. Mod Pathol. 2000; 13 (1): 29-36.

Bishop J A et al. Hum Pathol. 2013; 44 (10): 1982-1988.

Bourgeois J M et al. Am J Surg Pathol. 2000; 24 (7): 937-946.

Rubin B P et al Am J Pathol. 1998; 153 (5): 1451-1458.

Tognon C et al. Cancer Cell. 2002; 2:367-376.

Brzezianska E et al. Mutat Res. 2006; 599 (1-2): 26-35.

Fernandez-Cuesta L et al. 105th Annual Meeting of the American Association for Cancer Research, 2014, San Diego, California, AACR.

Leeman-Neill R J et al. Cancer. 2014; 120 (6): 799-807.

Ross J. S et al. Oncologist. 2014; 19 (3): 235-242.

Farago et al. JCO Precision Oncology. Published online Jul. 23, 2018.

Gatalica Z et al. Mod Pathol. Published online 23 Aug. 2018.

---

The invention claimed is:

1. A method of detecting a fusion protein of TrkA, TrkB, or TrkC in a non-neuroendocrine tumor sample, the method comprising:

affinity histochemically staining the sample with an antibody that specifically binds to an amino acid sequence comprising residues 363-760 of SEQ ID NO: 1, an amino acid sequence comprising residues 646-838 of SEQ ID NO: 2, and an amino acid sequence comprising residues 718-839 of SEQ ID NO: 3;

detecting nuclear staining in the sample; and scoring the sample as positive for a fusion protein involving TrkA, TrkB, or TrkC if the detected nuclear staining has a staining pattern which is greater than or equal to a threshold percentage of tumor cells within a threshold contiguous tumor cell area that are specifically stained above a threshold staining intensity, wherein the threshold contiguous tumor cell area is at least 20 contiguous cells, wherein the threshold percentage of tumor cells ranges from 25% to 75% or 25% to 80%.

2. The method of claim 1, wherein the threshold percentage of tumor cells is 50% and the threshold staining intensity is 1.75.

3. The method of claim 1, wherein the threshold percentage of tumor cells is 60% and the threshold staining intensity is 1.75.

4. The method of claim 1, wherein the threshold percentage of tumor cells is 75% and the threshold staining intensity is 1.75.

5. The method of claim 1, wherein the threshold percentage of tumor cells is 50% and the threshold staining intensity is 2.

6. The method of claim 1, wherein the threshold percentage of tumor cells is 60% and the threshold staining intensity is 2.

7. The method of claim 1, wherein the threshold percentage of tumor cells is 75% and the threshold staining intensity is 2.

8. The method of claim 1, wherein the threshold percentage of cells is in the range of 25% to 80%, and the threshold staining intensity is any specific staining above background.

9. The method of claim 1, wherein the threshold percentage of cells is in the range of 25% to 80%, and the threshold staining intensity is 0.5.

10. The method of claim 1, wherein the threshold level of contiguous tumor cells is at least 50 contiguous cells, and the threshold percentage of cells is 80%, and the threshold staining intensity is any specific staining above background.

11. The method of claim 1, wherein the threshold level of contiguous tumor cells is at least 50 contiguous cells, and the threshold percentage of cells is 80%, and the threshold staining intensity is 0.5.

12. The method of claim 1, wherein the affinity histochemically staining comprises: (a) subjecting the sample to a heat-induced epitope retrieval process; and (b) contacting the sample with the antibody and a set of detection reagents to deposit a brightfield dye in proximity to any antibody bound to the sample.

13. The method of claim 12, wherein the set of detection reagents comprises a secondary antibody immunoreactive with the antibody, a tertiary antibody immunoreactive with the secondary antibody conjugated to an enzyme, and a set of reagents reactive with the enzyme to effect deposition of a brightfield dye on the sample.

14. The method of claim 13, wherein the secondary antibody is haptenated and the tertiary antibody is an anti-hapten antibody.

15. The method of claim 12, wherein the brightfield dye is 3,3'-diaminobenzidine (DAB).

16. The method of claim 1, wherein the antibody specifically binds to an amino acid sequence comprising residues 363-760 of SEQ ID NO: 1 and an amino acid sequence comprising residues 646-838 of SEQ ID NO: 2.

17. The method of claim 1, wherein the antibody is EPR17341.

18. The method of claim 1, wherein the antibody is B-3.

19. The method of claim 1, wherein the threshold percentage of cells is in the range of between about 25% to 75%.

20. The method of claim 1, wherein the threshold staining intensity is any specific staining above background.

\* \* \* \* \*

SEQUENCE LISTING

```
<160> NUMBER OF SEQ ID NOS: 3

<210> SEQ ID NO 1
<211> LENGTH: 760
<212> TYPE: PRT
<213> ORGANISM: Homo sapiens

<400> SEQUENCE: 1

Met Lys Glu Ala Ala Leu Ile Cys Leu Ala Pro Ser Val Pro Pro Ile
1               5                   10                  15

Leu Thr Val Lys Ser Trp Asp Thr Met Gln Leu Arg Ala Ala Arg Ser
                20                  25                  30

Arg Cys Thr Asn Leu Leu Ala Ala Ser Tyr Ile Glu Asn Gln Gln His
            35                  40                  45

Leu Gln His Leu Glu Leu Arg Asp Leu Arg Gly Leu Gly Glu Leu Arg
        50                  55                  60

Asn Leu Thr Ile Val Lys Ser Gly Leu Arg Phe Val Ala Pro Asp Ala
65                  70                  75                  80

Phe His Phe Thr Pro Arg Leu Ser Arg Leu Asn Leu Ser Phe Asn Ala
                85                  90                  95

Leu Glu Ser Leu Ser Trp Lys Thr Val Gln Gly Leu Ser Leu Gln Glu
            100                 105                 110

Leu Val Leu Ser Gly Asn Pro Leu His Cys Ser Cys Ala Leu Arg Trp
        115                 120                 125

Leu Gln Arg Trp Glu Glu Glu Gly Leu Gly Gly Val Pro Glu Gln Lys
    130                 135                 140

Leu Gln Cys His Gly Gln Gly Pro Leu Ala His Met Pro Asn Ala Ser
145                 150                 155                 160

Cys Gly Val Pro Thr Leu Lys Val Gln Val Pro Asn Ala Ser Val Asp
                165                 170                 175

Val Gly Asp Asp Val Leu Leu Arg Cys Gln Val Glu Gly Arg Gly Leu
            180                 185                 190

Glu Gln Ala Gly Trp Ile Leu Thr Glu Leu Glu Gln Ser Ala Thr Val
        195                 200                 205

Met Lys Ser Gly Gly Leu Pro Ser Leu Gly Leu Thr Leu Ala Asn Val
    210                 215                 220

Thr Ser Asp Leu Asn Arg Lys Asn Val Thr Cys Trp Ala Glu Asn Asp
225                 230                 235                 240

Val Gly Arg Ala Glu Val Ser Val Gln Val Asn Val Ser Phe Pro Ala
                245                 250                 255

Ser Val Gln Leu His Thr Ala Val Glu Met His His Trp Cys Ile Pro
            260                 265                 270

Phe Ser Val Asp Gly Gln Pro Ala Pro Ser Leu Arg Trp Leu Phe Asn
```

-continued

```
                275                 280                 285

Gly Ser Val Leu Asn Glu Thr Ser Phe Ile Phe Thr Glu Phe Leu Glu
    290                 295                 300

Pro Ala Ala Asn Glu Thr Val Arg His Gly Cys Leu Arg Leu Asn Gln
305                 310                 315                 320

Pro Thr His Val Asn Asn Gly Asn Tyr Thr Leu Leu Ala Ala Asn Pro
                325                 330                 335

Phe Gly Gln Ala Ser Ala Ser Ile Met Ala Ala Phe Met Asp Asn Pro
                340                 345                 350

Phe Glu Phe Asn Pro Glu Asp Pro Ile Pro Asp Thr Asn Ser Thr Ser
                355                 360                 365

Gly Asp Pro Val Glu Lys Lys Asp Glu Thr Pro Phe Gly Val Ser Val
    370                 375                 380

Ala Val Gly Leu Ala Val Phe Ala Cys Leu Phe Leu Ser Thr Leu Leu
385                 390                 395                 400

Leu Val Leu Asn Lys Cys Gly Arg Arg Asn Lys Phe Gly Ile Asn Arg
                405                 410                 415

Pro Ala Val Leu Ala Pro Glu Asp Gly Leu Ala Met Ser Leu His Phe
                420                 425                 430

Met Thr Leu Gly Gly Ser Ser Leu Ser Pro Thr Glu Gly Lys Gly Ser
        435                 440                 445

Gly Leu Gln Gly His Ile Ile Glu Asn Pro Gln Tyr Phe Ser Asp Ala
    450                 455                 460

Cys Val His His Ile Lys Arg Arg Asp Ile Val Leu Lys Trp Glu Leu
465                 470                 475                 480

Gly Glu Gly Ala Phe Gly Lys Val Phe Leu Ala Glu Cys His Asn Leu
                485                 490                 495

Leu Pro Glu Gln Asp Lys Met Leu Val Ala Val Lys Ala Leu Lys Glu
                500                 505                 510

Ala Ser Glu Ser Ala Arg Gln Asp Phe Gln Arg Glu Ala Glu Leu Leu
                515                 520                 525

Thr Met Leu Gln His Gln His Ile Val Arg Phe Phe Gly Val Cys Thr
    530                 535                 540

Glu Gly Arg Pro Leu Leu Met Val Phe Glu Tyr Met Arg His Gly Asp
545                 550                 555                 560

Leu Asn Arg Phe Leu Arg Ser His Gly Pro Asp Ala Lys Leu Leu Ala
                565                 570                 575

Gly Gly Glu Asp Val Ala Pro Gly Pro Leu Gly Leu Gly Gln Leu Leu
                580                 585                 590

Ala Val Ala Ser Gln Val Ala Ala Gly Met Val Tyr Leu Ala Gly Leu
        595                 600                 605

His Phe Val His Arg Asp Leu Ala Thr Arg Asn Cys Leu Val Gly Gln
    610                 615                 620

Gly Leu Val Val Lys Ile Gly Asp Phe Gly Met Ser Arg Asp Ile Tyr
625                 630                 635                 640

Ser Thr Asp Tyr Tyr Arg Val Gly Gly Arg Thr Met Leu Pro Ile Arg
                645                 650                 655

Trp Met Pro Pro Glu Ser Ile Leu Tyr Arg Lys Phe Thr Thr Glu Ser
        660                 665                 670

Asp Val Trp Ser Phe Gly Val Val Leu Trp Glu Ile Phe Thr Tyr Gly
        675                 680                 685

Lys Gln Pro Trp Tyr Gln Leu Ser Asn Thr Glu Ala Ile Asp Cys Ile
    690                 695                 700
```

```
Thr Gln Gly Arg Glu Leu Glu Arg Pro Arg Ala Cys Pro Pro Glu Val
705             710             715             720

Tyr Ala Ile Met Arg Gly Cys Trp Gln Arg Glu Pro Gln Gln Arg His
            725             730             735

Ser Ile Lys Asp Val His Ala Arg Leu Gln Ala Leu Ala Gln Ala Pro
            740             745             750

Pro Val Tyr Leu Asp Val Leu Gly
            755             760

<210> SEQ ID NO 2
<211> LENGTH: 838
<212> TYPE: PRT
<213> ORGANISM: Homo sapiens

<400> SEQUENCE: 2

Met Ser Ser Trp Ile Arg Trp His Gly Pro Ala Met Ala Arg Leu Trp
1               5               10              15

Gly Phe Cys Trp Leu Val Val Gly Phe Trp Arg Ala Ala Phe Ala Cys
            20              25              30

Pro Thr Ser Cys Lys Cys Ser Ala Ser Arg Ile Trp Cys Ser Asp Pro
            35              40              45

Ser Pro Gly Ile Val Ala Phe Pro Arg Leu Glu Pro Asn Ser Val Asp
        50              55              60

Pro Glu Asn Ile Thr Glu Ile Phe Ile Ala Asn Gln Lys Arg Leu Glu
65              70              75              80

Ile Ile Asn Glu Asp Asp Val Glu Ala Tyr Val Gly Leu Arg Asn Leu
                85              90              95

Thr Ile Val Asp Ser Gly Leu Lys Phe Val Ala His Lys Ala Phe Leu
            100             105             110

Lys Asn Ser Asn Leu Gln His Ile Asn Phe Thr Arg Asn Lys Leu Thr
        115             120             125

Ser Leu Ser Arg Lys His Phe Arg His Leu Asp Leu Ser Glu Leu Ile
        130             135             140

Leu Val Gly Asn Pro Phe Thr Cys Ser Cys Asp Ile Met Trp Ile Lys
145             150             155             160

Thr Leu Gln Glu Ala Lys Ser Ser Pro Asp Thr Gln Asp Leu Tyr Cys
            165             170             175

Leu Asn Glu Ser Ser Lys Asn Ile Pro Leu Ala Asn Leu Gln Ile Pro
            180             185             190

Asn Cys Gly Leu Pro Ser Ala Asn Leu Ala Ala Pro Asn Leu Thr Val
            195             200             205

Glu Glu Gly Lys Ser Ile Thr Leu Ser Cys Ser Val Ala Gly Asp Pro
        210             215             220

Val Pro Asn Met Tyr Trp Asp Val Gly Asn Leu Val Ser Lys His Met
225             230             235             240

Asn Glu Thr Ser His Thr Gln Gly Ser Leu Arg Ile Thr Asn Ile Ser
            245             250             255

Ser Asp Asp Ser Gly Lys Gln Ile Ser Cys Val Ala Glu Asn Leu Val
            260             265             270

Gly Glu Asp Gln Asp Ser Val Asn Leu Thr Val His Phe Ala Pro Thr
            275             280             285

Ile Thr Phe Leu Glu Ser Pro Thr Ser Asp His His Trp Cys Ile Pro
        290             295             300

Phe Thr Val Lys Gly Asn Pro Lys Pro Ala Leu Gln Trp Phe Tyr Asn
```

```
305                310                315                320

Gly Ala Ile Leu Asn Glu Ser Lys Tyr Ile Cys Thr Lys Ile His Val
                325                330                335

Thr Asn His Thr Glu Tyr His Gly Cys Leu Gln Leu Asp Asn Pro Thr
            340                345                350

His Met Asn Asn Gly Asp Tyr Thr Leu Ile Ala Lys Asn Glu Tyr Gly
        355                360                365

Lys Asp Glu Lys Gln Ile Ser Ala His Phe Met Gly Trp Pro Gly Ile
    370                375                380

Asp Asp Gly Ala Asn Pro Asn Tyr Pro Asp Val Ile Tyr Glu Asp Tyr
385                390                395                400

Gly Thr Ala Ala Asn Asp Ile Gly Asp Thr Thr Asn Arg Ser Asn Glu
                405                410                415

Ile Pro Ser Thr Asp Val Thr Asp Lys Thr Gly Arg Glu His Leu Ser
            420                425                430

Val Tyr Ala Val Val Val Ile Ala Ser Val Val Gly Phe Cys Leu Leu
        435                440                445

Val Met Leu Phe Leu Leu Lys Leu Ala Arg His Ser Lys Phe Gly Met
    450                455                460

Lys Asp Phe Ser Trp Phe Gly Phe Gly Lys Val Lys Ser Arg Gln Gly
465                470                475                480

Val Gly Pro Ala Ser Val Ile Ser Asn Asp Asp Asp Ser Ala Ser Pro
                485                490                495

Leu His His Ile Ser Asn Gly Ser Asn Thr Pro Ser Ser Ser Glu Gly
            500                505                510

Gly Pro Asp Ala Val Ile Ile Gly Met Thr Lys Ile Pro Val Ile Glu
        515                520                525

Asn Pro Gln Tyr Phe Gly Ile Thr Asn Ser Gln Leu Lys Pro Asp Thr
    530                535                540

Phe Val Gln His Ile Lys Arg His Asn Ile Val Leu Lys Arg Glu Leu
545                550                555                560

Gly Glu Gly Ala Phe Gly Lys Val Phe Leu Ala Glu Cys Tyr Asn Leu
                565                570                575

Cys Pro Glu Gln Asp Lys Ile Leu Val Ala Val Lys Thr Leu Lys Asp
            580                585                590

Ala Ser Asp Asn Ala Arg Lys Asp Phe His Arg Glu Ala Glu Leu Leu
        595                600                605

Thr Asn Leu Gln His Glu His Ile Val Lys Phe Tyr Gly Val Cys Val
    610                615                620

Glu Gly Asp Pro Leu Ile Met Val Phe Glu Tyr Met Lys His Gly Asp
625                630                635                640

Leu Asn Lys Phe Leu Arg Ala His Gly Pro Asp Ala Val Leu Met Ala
                645                650                655

Glu Gly Asn Pro Pro Thr Glu Leu Thr Gln Ser Gln Met Leu His Ile
            660                665                670

Ala Gln Gln Ile Ala Ala Gly Met Val Tyr Leu Ala Ser Gln His Phe
        675                680                685

Val His Arg Asp Leu Ala Thr Arg Asn Cys Leu Val Gly Glu Asn Leu
    690                695                700

Leu Val Lys Ile Gly Asp Phe Gly Met Ser Arg Asp Val Tyr Ser Thr
705                710                715                720

Asp Tyr Tyr Arg Val Gly Gly His Thr Met Leu Pro Ile Arg Trp Met
                725                730                735
```

-continued

```
Pro Pro Glu Ser Ile Met Tyr Arg Lys Phe Thr Thr Glu Ser Asp Val
        740             745             750

Trp Ser Leu Gly Val Val Leu Trp Glu Ile Phe Thr Tyr Gly Lys Gln
        755             760             765

Pro Trp Tyr Gln Leu Ser Asn Asn Glu Val Ile Glu Cys Ile Thr Gln
    770             775             780

Gly Arg Val Leu Gln Arg Pro Arg Thr Cys Pro Gln Glu Val Tyr Glu
785             790             795             800

Leu Met Leu Gly Cys Trp Gln Arg Glu Pro His Met Arg Lys Asn Ile
            805             810             815

Lys Gly Ile His Thr Leu Leu Gln Asn Leu Ala Lys Ala Ser Pro Val
            820             825             830

Tyr Leu Asp Ile Leu Gly
            835

<210> SEQ ID NO 3
<211> LENGTH: 839
<212> TYPE: PRT
<213> ORGANISM: Homo sapiens

<400> SEQUENCE: 3

Met Asp Val Ser Leu Cys Pro Ala Lys Cys Ser Phe Trp Arg Ile Phe
1               5               10              15

Leu Leu Gly Ser Val Trp Leu Asp Tyr Val Gly Ser Val Leu Ala Cys
            20              25              30

Pro Ala Asn Cys Val Cys Ser Lys Thr Glu Ile Asn Cys Arg Arg Pro
            35              40              45

Asp Asp Gly Asn Leu Phe Pro Leu Leu Glu Gly Gln Asp Ser Gly Asn
        50              55              60

Ser Asn Gly Asn Ala Ser Ile Asn Ile Thr Asp Ile Ser Arg Asn Ile
65              70              75              80

Thr Ser Ile His Ile Glu Asn Trp Arg Ser Leu His Thr Leu Asn Ala
                85              90              95

Val Asp Met Glu Leu Tyr Thr Gly Leu Gln Lys Leu Thr Ile Lys Asn
            100             105             110

Ser Gly Leu Arg Ser Ile Gln Pro Arg Ala Phe Ala Lys Asn Pro His
        115             120             125

Leu Arg Tyr Ile Asn Leu Ser Ser Asn Arg Leu Thr Thr Leu Ser Trp
    130             135             140

Gln Leu Phe Gln Thr Leu Ser Leu Arg Glu Leu Gln Leu Glu Gln Asn
145             150             155             160

Phe Phe Asn Cys Ser Cys Asp Ile Arg Trp Met Gln Leu Trp Gln Glu
            165             170             175

Gln Gly Glu Ala Lys Leu Asn Ser Gln Asn Leu Tyr Cys Ile Asn Ala
            180             185             190

Asp Gly Ser Gln Leu Pro Leu Phe Arg Met Asn Ile Ser Gln Cys Asp
        195             200             205

Leu Pro Glu Ile Ser Val Ser His Val Asn Leu Thr Val Arg Glu Gly
    210             215             220

Asp Asn Ala Val Ile Thr Cys Asn Gly Ser Gly Ser Pro Leu Pro Asp
225             230             235             240

Val Asp Trp Ile Val Thr Gly Leu Gln Ser Ile Asn Thr His Gln Thr
            245             250             255

Asn Leu Asn Trp Thr Asn Val His Ala Ile Asn Leu Thr Leu Val Asn
```

-continued

```
                260               265               270
Val Thr Ser Glu Asp Asn Gly Phe Thr Leu Thr Cys Ile Ala Glu Asn
            275               280               285

Val Val Gly Met Ser Asn Ala Ser Val Ala Leu Thr Val Tyr Tyr Pro
        290               295               300

Pro Arg Val Val Ser Leu Glu Glu Pro Glu Leu Arg Leu Glu His Cys
305               310               315               320

Ile Glu Phe Val Val Arg Gly Asn Pro Pro Thr Leu His Trp Leu
            325               330               335

His Asn Gly Gln Pro Leu Arg Glu Ser Lys Ile Ile His Val Glu Tyr
            340               345               350

Tyr Gln Glu Gly Glu Ile Ser Glu Gly Cys Leu Leu Phe Asn Lys Pro
        355               360               365

Thr His Tyr Asn Asn Gly Asn Tyr Thr Leu Ile Ala Lys Asn Pro Leu
        370               375               380

Gly Thr Ala Asn Gln Thr Ile Asn Gly His Phe Leu Lys Glu Pro Phe
385               390               395               400

Pro Glu Ser Thr Asp Asn Phe Ile Leu Phe Asp Glu Val Ser Pro Thr
            405               410               415

Pro Pro Ile Thr Val Thr His Lys Pro Glu Glu Asp Thr Phe Gly Val
            420               425               430

Ser Ile Ala Val Gly Leu Ala Ala Phe Ala Cys Val Leu Leu Val Val
            435               440               445

Leu Phe Val Met Ile Asn Lys Tyr Gly Arg Arg Ser Lys Phe Gly Met
        450               455               460

Lys Gly Pro Val Ala Val Ile Ser Gly Glu Glu Asp Ser Ala Ser Pro
465               470               475               480

Leu His His Ile Asn His Gly Ile Thr Thr Pro Ser Ser Leu Asp Ala
            485               490               495

Gly Pro Asp Thr Val Val Ile Gly Met Thr Arg Ile Pro Val Ile Glu
            500               505               510

Asn Pro Gln Tyr Phe Arg Gln Gly His Asn Cys His Lys Pro Asp Thr
            515               520               525

Tyr Val Gln His Ile Lys Arg Arg Asp Ile Val Leu Lys Arg Glu Leu
        530               535               540

Gly Glu Gly Ala Phe Gly Lys Val Phe Leu Ala Glu Cys Tyr Asn Leu
545               550               555               560

Ser Pro Thr Lys Asp Lys Met Leu Val Ala Val Lys Ala Leu Lys Asp
            565               570               575

Pro Thr Leu Ala Ala Arg Lys Asp Phe Gln Arg Glu Ala Glu Leu Leu
            580               585               590

Thr Asn Leu Gln His Glu His Ile Val Lys Phe Tyr Gly Val Cys Gly
        595               600               605

Asp Gly Asp Pro Leu Ile Met Val Phe Glu Tyr Met Lys His Gly Asp
        610               615               620

Leu Asn Lys Phe Leu Arg Ala His Gly Pro Asp Ala Met Ile Leu Val
625               630               635               640

Asp Gly Gln Pro Arg Gln Ala Lys Gly Glu Leu Gly Leu Ser Gln Met
            645               650               655

Leu His Ile Ala Ser Gln Ile Ala Ser Gly Met Val Tyr Leu Ala Ser
            660               665               670

Gln His Phe Val His Arg Asp Leu Ala Thr Arg Asn Cys Leu Val Gly
            675               680               685
```

-continued

```
Ala Asn Leu Leu Val Lys Ile Gly Asp Phe Gly Met Ser Arg Asp Val
    690             695             700

Tyr Ser Thr Asp Tyr Tyr Arg Leu Phe Asn Pro Ser Gly Asn Asp Phe
705             710             715             720

Cys Ile Trp Cys Glu Val Gly Gly His Thr Met Leu Pro Ile Arg Trp
            725             730             735

Met Pro Pro Glu Ser Ile Met Tyr Arg Lys Phe Thr Thr Glu Ser Asp
            740             745             750

Val Trp Ser Phe Gly Val Ile Leu Trp Glu Ile Phe Thr Tyr Gly Lys
        755             760             765

Gln Pro Trp Phe Gln Leu Ser Asn Thr Glu Val Ile Glu Cys Ile Thr
    770             775             780

Gln Gly Arg Val Leu Glu Arg Pro Arg Val Cys Pro Lys Glu Val Tyr
785             790             795             800

Asp Val Met Leu Gly Cys Trp Gln Arg Glu Pro Gln Gln Arg Leu Asn
            805             810             815

Ile Lys Glu Ile Tyr Lys Ile Leu His Ala Leu Gly Lys Ala Thr Pro
            820             825             830

Ile Tyr Leu Asp Ile Leu Gly
            835
```